(12) United States Patent
Warner et al.

(10) Patent No.: US 9,394,299 B2
(45) Date of Patent: Jul. 19, 2016

(54) RILYAZINE DERIVATIVES AND COMPOSITIONS FOR THE TREATMENT OF CANCER

(71) Applicant: Warner Babcock Institute for Green Chemistry, LLC, Wilmington, MA (US)

(72) Inventors: John C. Warner, Wilmington, MA (US); Jeffery A. Gladding, Burlington, MA (US); Thomas W. Gero, Stow, MA (US); Srinivasa R. Cheruku, Lexington, MA (US)

(73) Assignee: Warner Babcock Institute for Green Chemistry, LLC, Wilmington, MA (US)

( * ) Notice: Subject to any disclaimer, the term of this patent is extended or adjusted under 35 U.S.C. 154(b) by 0 days.

(21) Appl. No.: 14/473,472

(22) Filed: Aug. 29, 2014

(65) Prior Publication Data
US 2015/0065510 A1  Mar. 5, 2015

Related U.S. Application Data

(60) Provisional application No. 61/874,039, filed on Sep. 5, 2013.

(51) Int. Cl.
*C07D 471/04* (2006.01)
(52) U.S. Cl.
CPC ..................... *C07D 471/04* (2013.01)

(58) Field of Classification Search
CPC .................................................... C07D 471/04
USPC .......................................... 514/248; 544/236
See application file for complete search history.

(56) References Cited

U.S. PATENT DOCUMENTS

2008/0269234 A1   10/2008   Gandhi et al.

FOREIGN PATENT DOCUMENTS

EP          1477175 A1     11/2004
WO     WO2012/097479 A1    7/2012

OTHER PUBLICATIONS

McMahon et al (2000).*
Pinedo et al. (2000).*
Epsztajn, J., et al., "Application of Organolithium and Related Reagents in Aynthesis, Part XII[1]. Synthesis of Phenyl- and Pyridylpyrido-pyridazinones and their Derivatives," Monatshefte fuer Chemie 1993;124:549-558.
International Search Report for PCT Patent App. No. PCT/US2014/053529 (Oct. 30, 2014).
International Preliminary Report on Patentability for PCT Patent App. No. PCT/US2014/053529 (Mar. 8, 2016).

* cited by examiner

*Primary Examiner* — Paul V Ward
(74) *Attorney, Agent, or Firm* — Cermak Nakajima & McGowan LLP; Malcolm K. McGowan

(57) ABSTRACT

The present application discloses Rilyazine analogs, methods for their preparation, and the treatment of cancer by the administration of an effective amount of the Rilyazine analogs to a patient in need thereof.

9 Claims, 11 Drawing Sheets

Figure 1: Results of biological screening of RL-1 using the NCI in single point dosing at 10 µM.
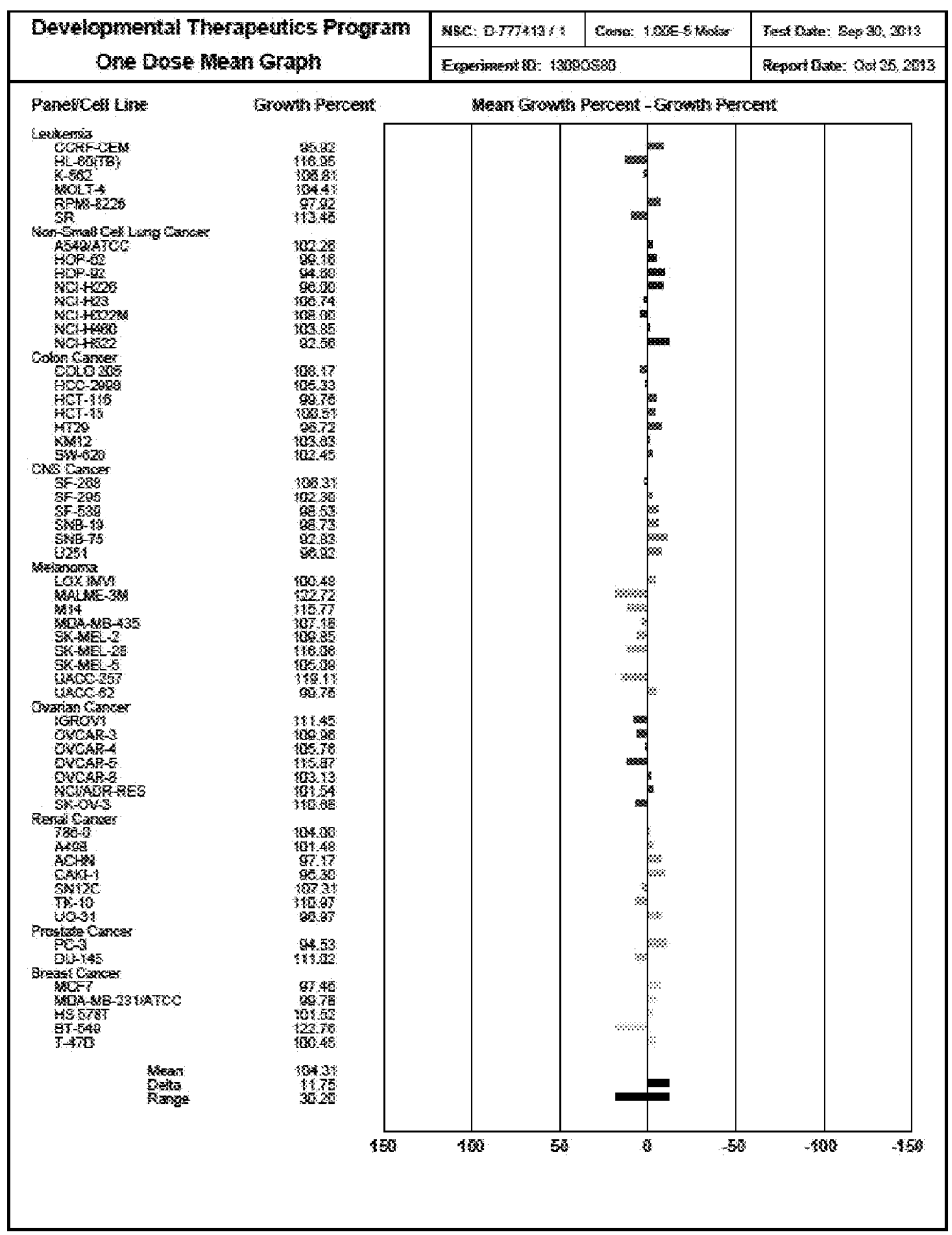

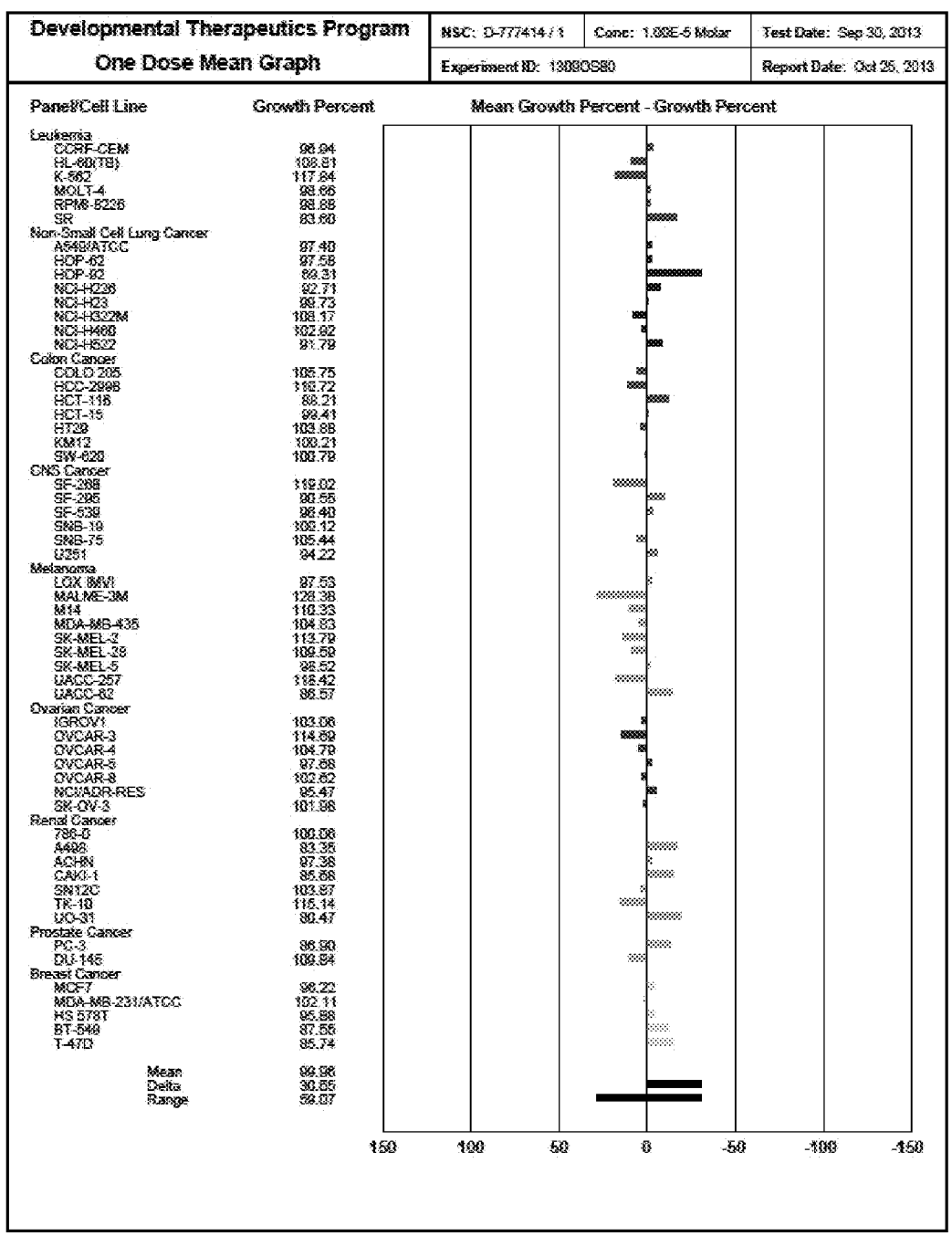
Figure 2: Results of biological screening of RL-2 using the NCI in single point dosing at 10 μM.

Figure 3: Results of biological screening of RL-3 using the NCI in single point dosing at 10 µM.
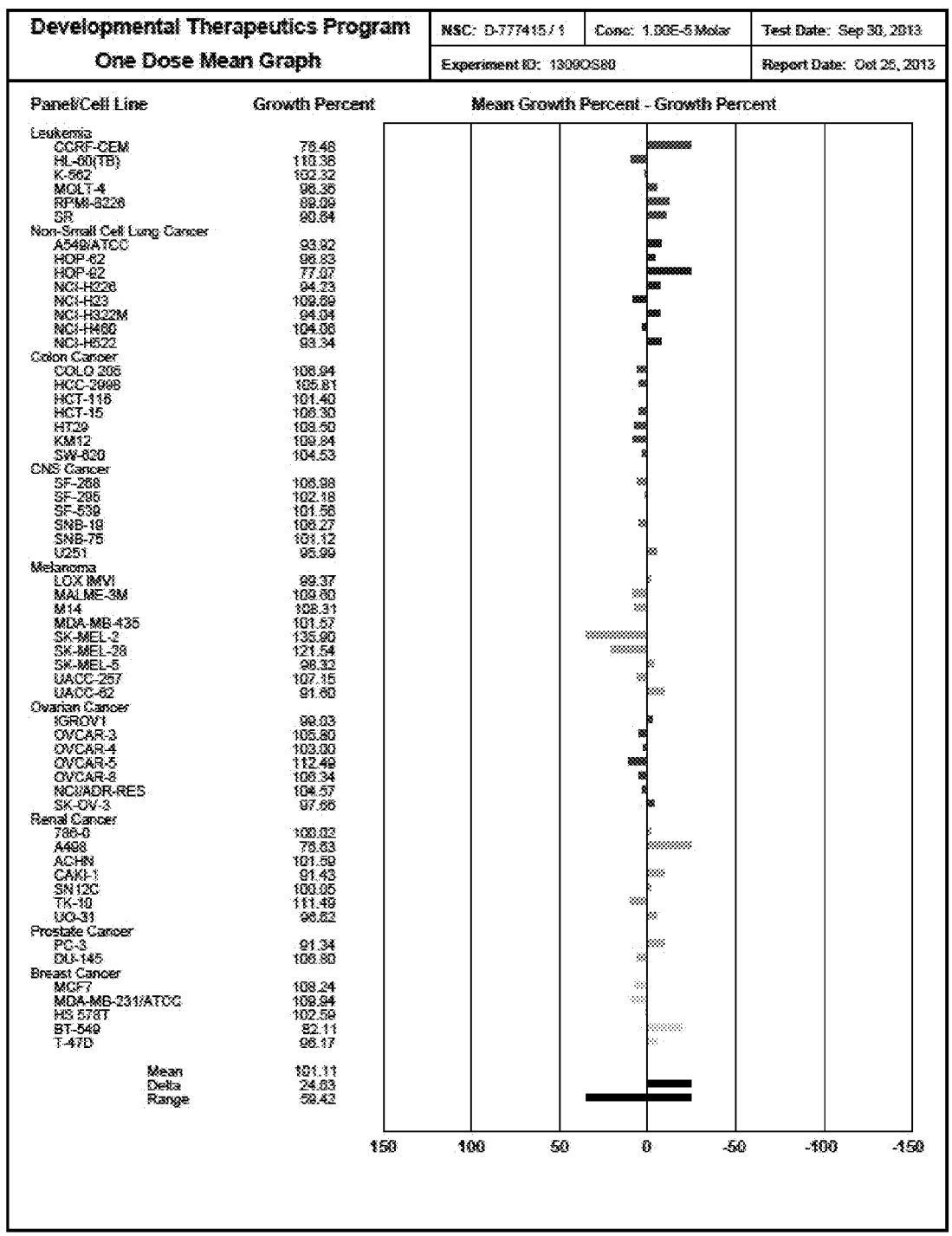

Figure 4: Representative results of biological screening of RL-4 using the NCI in single point dosing at 10 µM.
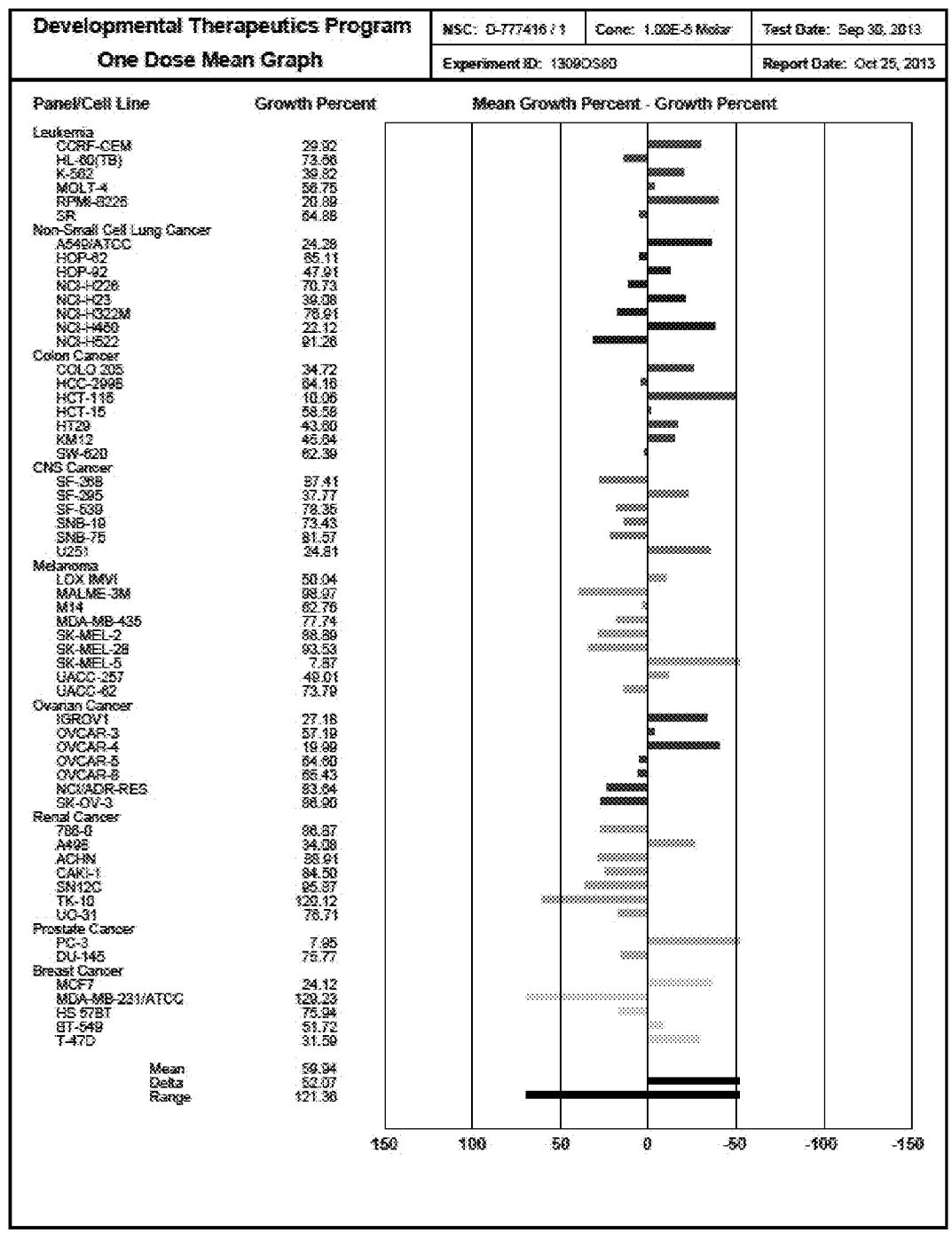

Figure 5: Results of biological screening of RL-4 using the NCI in five point dosing at $10^{-8}$ M, $10^{-7}$ M, $10^{-6}$ M, $10^{-5}$ M, and $10^{-4}$ M.

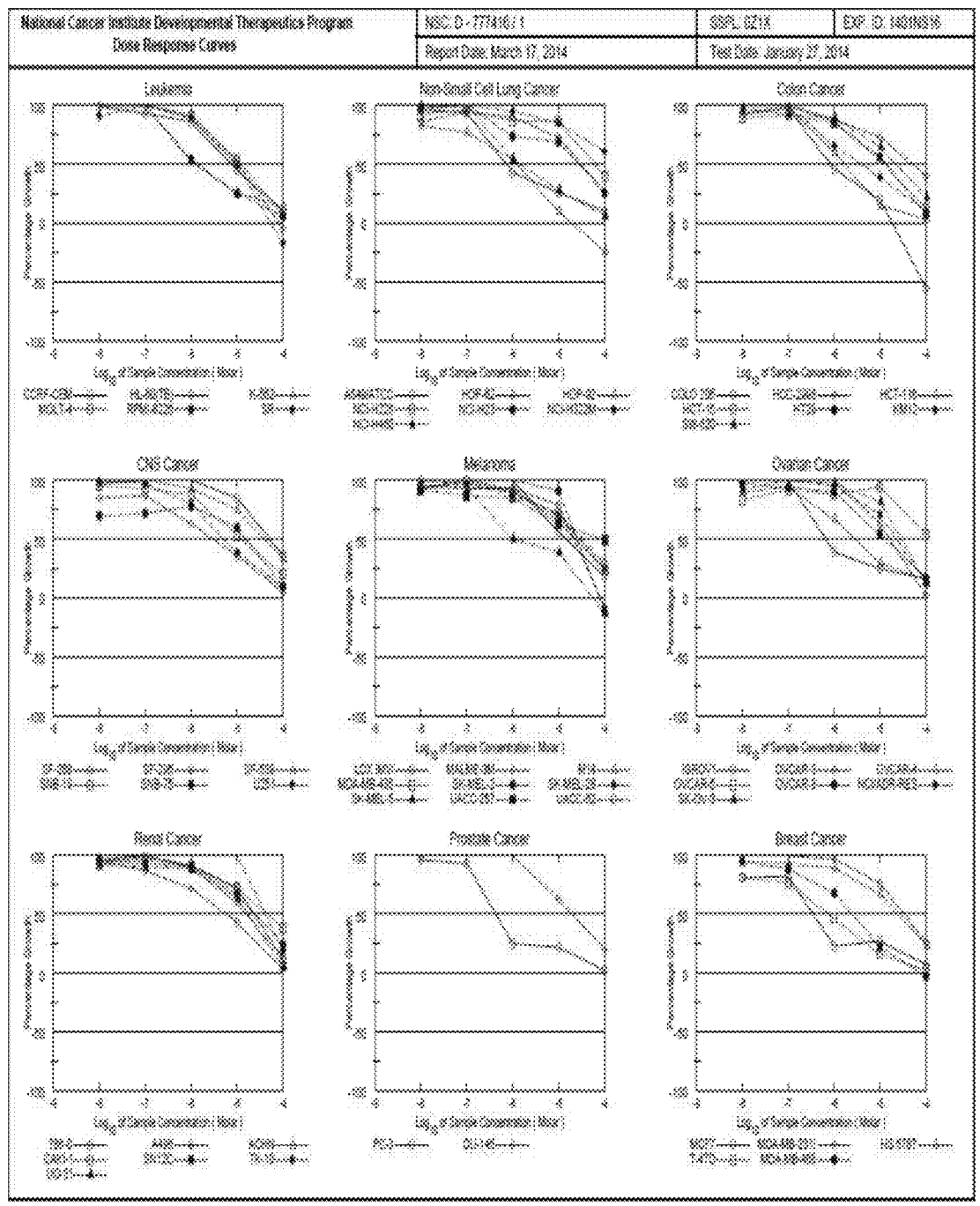
Figure 6: Dose Response Curves resulting from biological screening of RL-4 using the NCI in five point dosing at $10^{-8}$ M, $10^{-7}$ M, $10^{-6}$ M, $10^{-5}$ M, and $10^{-4}$ M showing Growth Percent as a function of concentration of RL-4. Data are shown for all 60 cell lines are grouped by panel, i.e., type of cancer.

Figure 7: GI50, TGI, and LC50 resulting from biological screening of RL-4 using the NCI in five point dosing at $10^{-8}$ M, $10^{-7}$ M, $10^{-6}$ M, $10^{-5}$ M, and $10^{-4}$ M. Mean, Delta and Range are given across all cell lines for the three parameters GI50, TGI, and LC50. Mean graphs plot the deviation of the value for each cell line from the mean across all cell lines.

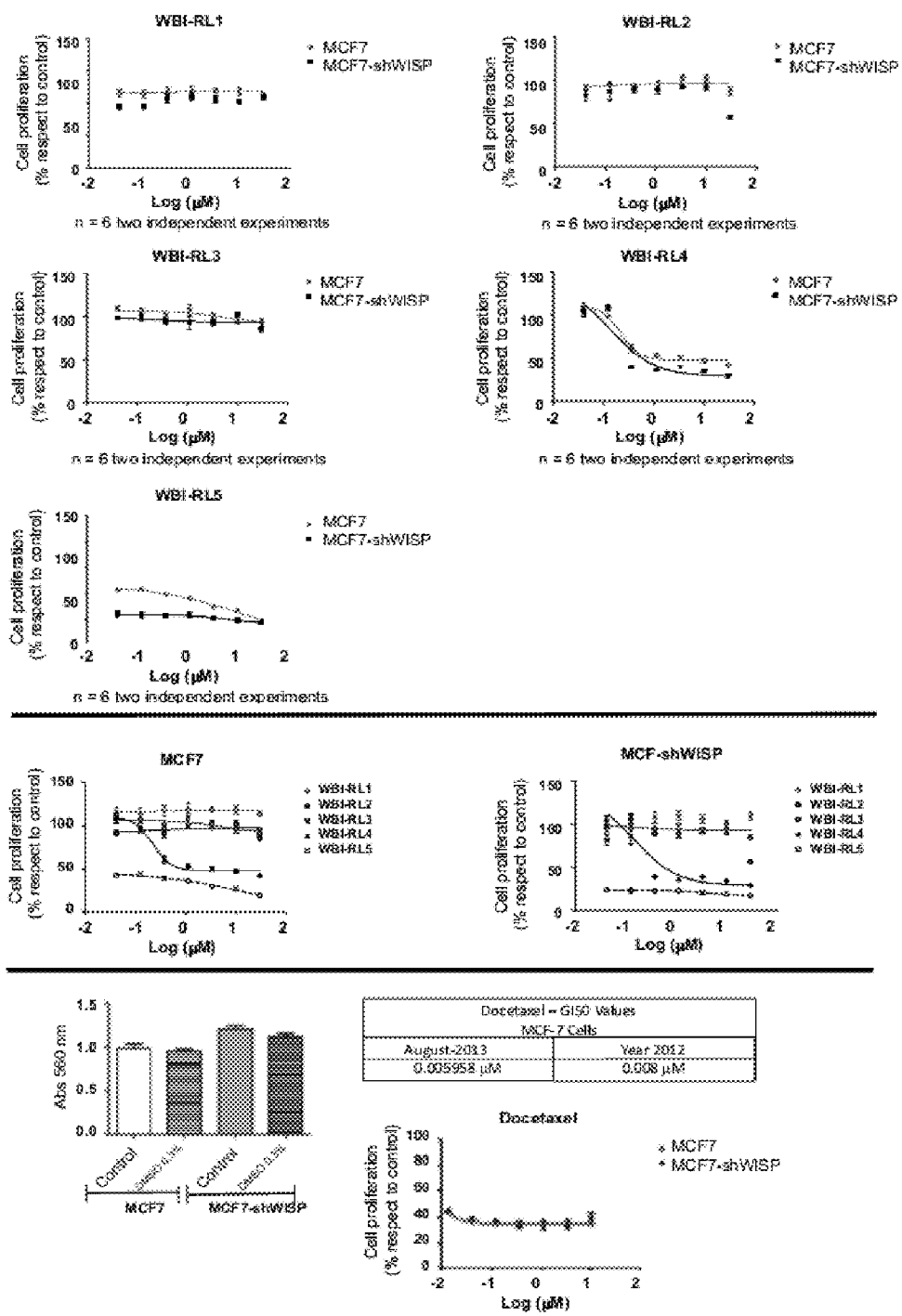
Figure 8: MCF-7 and MCF-shWisp Models

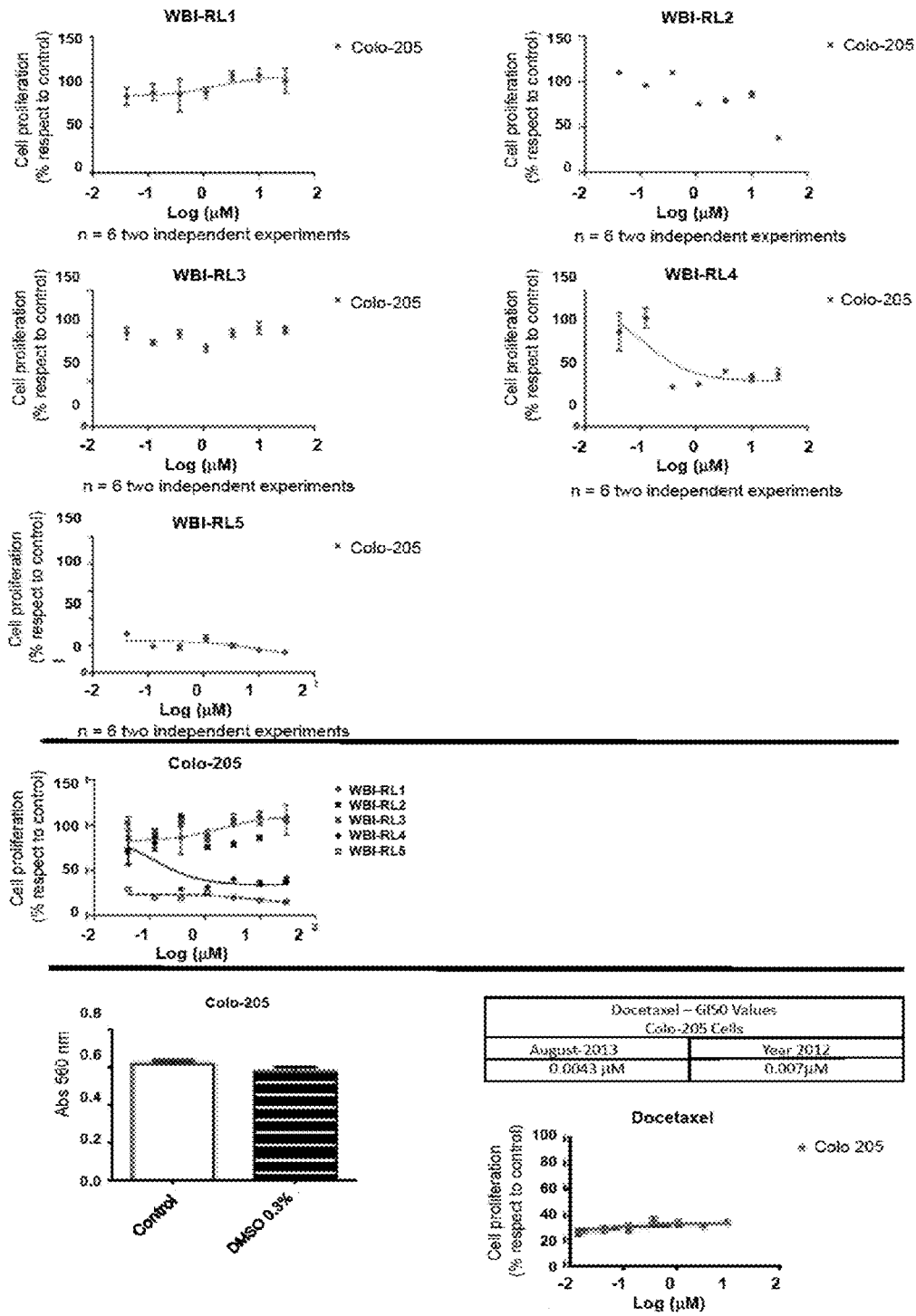
Figure 9: Colo-205 Model

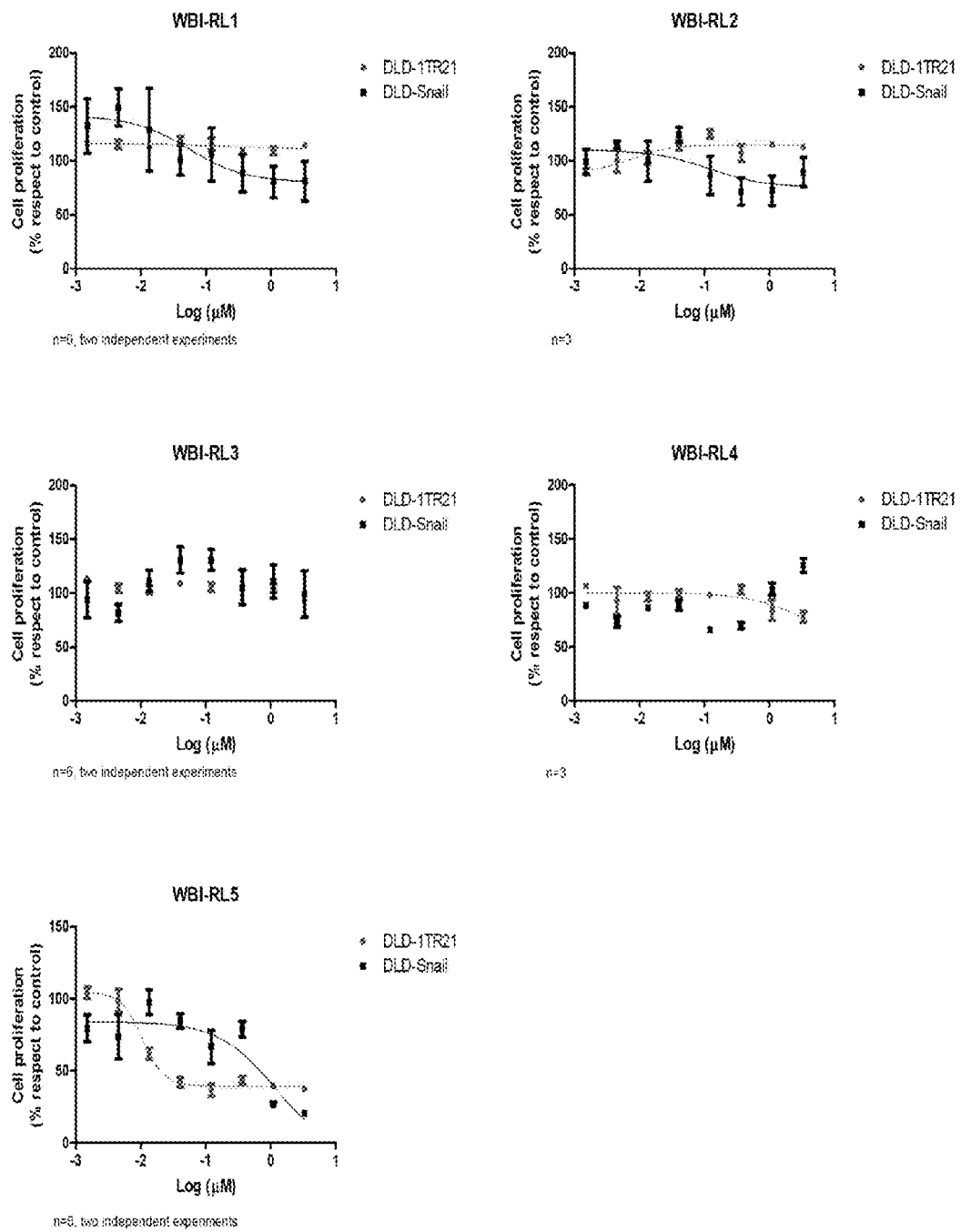
Figure 10: Cell Proliferation Assay results using DLD-1TR21 and DLD-Snail models.

Figure 11: Cell Proliferation Assay results using DLD-1TR21 and DLD-Snail models.
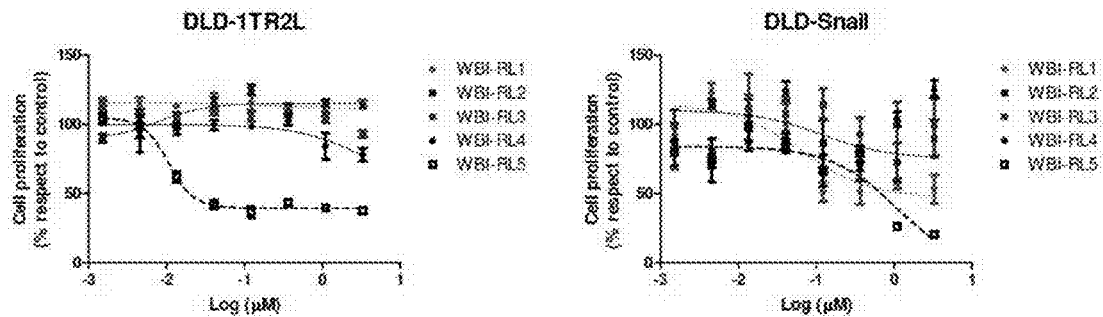
Figure 12: Ortep Drawings of X-Ray Crystallographic Structures of RL-3 and RL-4.
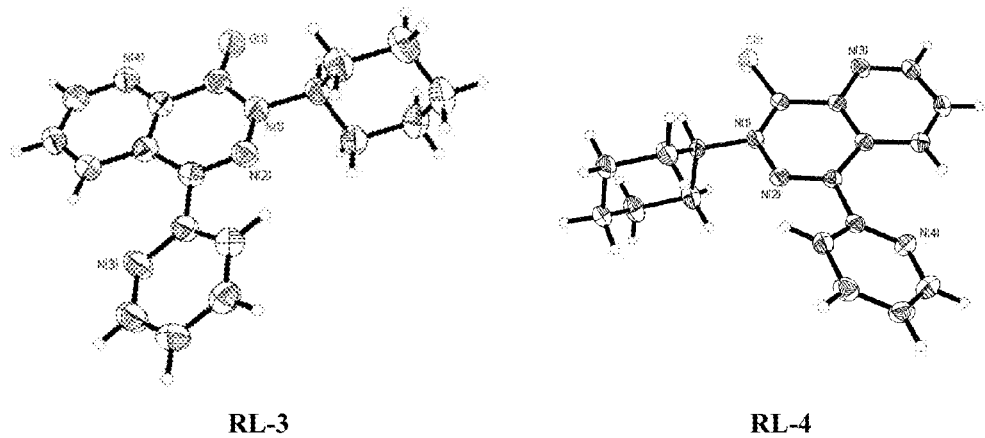

RILYAZINE DERIVATIVES AND COMPOSITIONS FOR THE TREATMENT OF CANCER

RELATED APPLICATION

This application claims the benefit of U.S. Provisional Application No. 61/874,039 filed Sep. 5, 2013.

SUMMARY OF THE INVENTION

There is a continuing need for selective, active anticancer and antitumor agents with improved therapeutic indices relative to the arsenal of cytotoxic agents currently available for cancer therapy. Such compounds have the potential to reduce untoward, sometimes debilitating, and dose-limiting, side-effects whilst still maintaining anticancer activity. In pursuit of this, we disclose a novel series of compounds that have excellent potential as potent antineoplastic agents with a significantly reduced toxicity profile. The following embodiments, aspects and variations thereof are exemplary and illustrative are not intended to be limiting in scope.

In one embodiment of the invention, the application discloses a compound selected from the group consisting of:

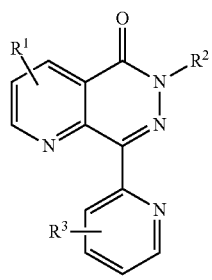

RL-A

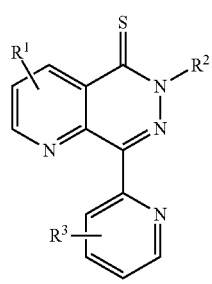

RL-B

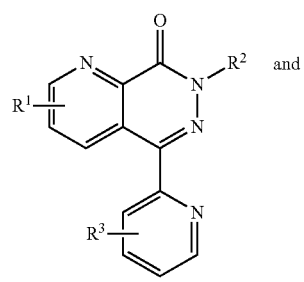

RL-C and

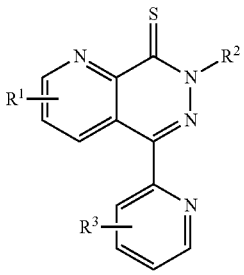

RL-D wherein:
each $R^1$ is independently selected from the group consisting of hydrogen, halo, nitro, trifluoromethyl, trifluoromethoxy, methoxy, carboxy, —$NH_2$, —OH, —SH, —$NHCH_3$, —$N(CH_3)_2$, —$SCH_3$, —CN, ($C_1$-$C_6$)alkyl, substituted ($C_1$-$C_6$)alkyl, aryl and heteroaryl;

each $R^2$ is independently selected from the group consisting of hydrogen, ($C_1$-$C_{12}$)alkyl, ($C_1$-$C_{12}$)alkoxy, —C(O)($C_1$-$C_{12}$)alkyl, ($C_3$-$C_{10}$)cycloalkyl, aryl, aryloxy, heteroaryl and heteroaryloxy, wherein each of ($C_1$-$C_{12}$)alkyl, ($C_1$-$C_{12}$)alkoxy, —C(O)($C_1$-$C_{12}$)alkyl, ($C_3$-$C_{10}$)cycloalkyl, aryl, aryloxy, heteroaryl and heteroaryloxy is unsubstituted or substituted with 1 or 2 substituents selected from the group consisting of halo, nitro, trifluoromethyl, trifluoromethoxy, methoxy, carboxy, —$NH_2$, —OH, —SH, —$NHCH_3$, —$N(CH_3)_2$, —$SCH_3$, —CN, ($C_1$-$C_6$)alkyl, substituted ($C_1$-$C_6$)alkyl, aryl and heteroaryl; and each $R^3$ is independently selected from the group consisting of hydrogen, halo, nitro, trifluoromethyl, trifluoromethoxy, methoxy, carboxy, —$NH_2$, —OH, —SH, —$NHCH_3$, —$N(CH_3)_2$, —$SCH_3$, —CN, ($C_1$-$C_6$)alkyl, substituted ($C_1$-$C_6$)alkyl, aryl and heteroaryl.

In one aspect of the above embodiment, the application discloses the above compound, where each $R^2$ is independently selected from the group consisting of ($C_1$-$C_{12}$)alkyl, ($C_1$-$C_{12}$)alkyl-aryl, ($C_1$-$C_{12}$)alkoxy, —C(O)($C_1$-$C_{12}$)alkyl, ($C_3$-$C_{10}$)cycloalkyl, aryl and heteroaryl, wherein each of ($C_1$-$C_{12}$)alkyl, ($C_1$-$C_{12}$)alkoxy, —C(O)($C_1$-$C_{12}$)alkyl, ($C_3$-$C_{10}$) cycloalkyl, aryl and heteroaryl is unsubstituted or substituted with 1 or 2 substituents selected from the group consisting of ($C_1$-$C_6$)alkyl, halo, nitro, trifluoromethyl, trifluoromethoxy, methoxy, carboxy, —$NH_2$, —OH, —SH, —$NHCH_3$, —$N(CH_3)_2$, —$SCH_3$, —CN, ($C_1$-$C_6$)alkyl, substituted ($C_1$-$C_6$)alkyl, aryl and heteroaryl. In one aspect of the above, each $R^2$ is independently a cyclyl group, a heterocyclyl group or an arylalkyl group.

In another aspect of this embodiment, the application discloses the above compound where:
each $R^1$ is independently selected from the group consisting of ($C_1$-$C_6$)alkyl, substituted ($C_1$-$C_6$)alkyl, aryl and heteroaryl;

each $R^2$ is independently selected from the group consisting of ($C_1$-$C_{12}$)alkyl, ($C_1$-$C_{12}$)alkyl-aryl, ($C_1$-$C_{12}$)alkoxy, —C(O)($C_1$-$C_{12}$)alkyl, ($C_3$-$C_{10}$)cycloalkyl, aryl, aryloxy, heteroaryl and heteroaryloxy, wherein each of ($C_1$-$C_{12}$)alkyl, ($C_1$-$C_{12}$)alkoxy, —C(O)($C_1$-$C_{12}$)alkyl, ($C_3$-$C_{10}$)cycloalkyl, aryl, aryloxy, heteroaryl and heteroaryloxy is unsubstituted or substituted with 1 or 2 substituents selected from the group consisting of halo, nitro, trifluoromethyl, trifluoromethoxy, methoxy, carboxy, —NH₂, —OH, —SH, —NHCH₃, —N(CH₃)₂, —SCH₃, —CN, (C₁-C₆)alkyl, substituted (C₁-C₆)alkyl, aryl and heteroaryl; and each $R^3$ is independently selected from the group consisting of halo, nitro, trifluoromethyl, trifluoromethoxy, methoxy, carboxy, —NH₂, —OH, —SH, —NHCH₃, —N(CH₃)₂, —SCH₃, —CN, (C₁-C₆)alkyl, substituted (C₁-C₆)alkyl, aryl and heteroaryl.

In another aspect of the above embodiment, the application discloses the above compound wherein: $R^1$ and $R^3$ are each hydrogen; and each $R^2$ is independently selected from the group consisting of:

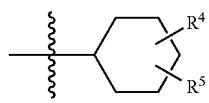

wherein $R^4$ and $R^5$ are each independently hydrogen, (C₁-C₆)alkyl, F, Cl, Br, I, nitro, trifluoromethyl, trifluoromethoxy, methoxy, carboxy, —NH₂, —OH, —SH, —NHCH₃, —N(CH₃)₂, —SCH₃ and —CN. In another aspect of the above compound, $R^4$ is hydrogen; and $R^5$ is 2-, 3- or 4-substituted with (C₁-C₃)alkyl; as a single isomer or mixture of stereoisomers.

In yet another aspect of this embodiment, the application discloses a compound selected from the group consisting of:

RL-1

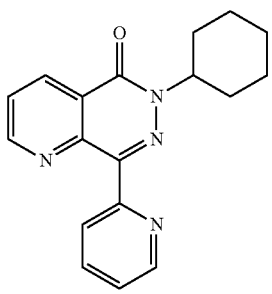

RL-2

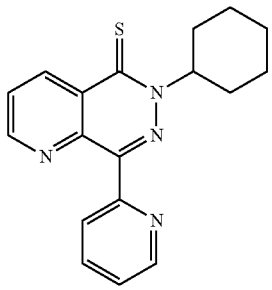

RL-3

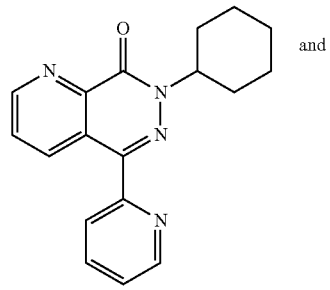

and

RL-4

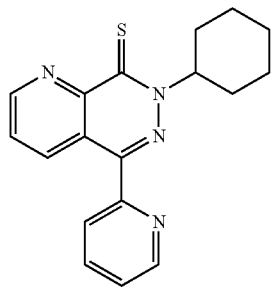

The above compounds include 6-cyclohexyl-8-(pyridin-2-yl)pyrido[2,3-d]pyridazin-5(6H)-one (RL-1) and the corresponding thione (RL-2); 7-cyclohexyl-5-(pyridin-2-yl)pyrido[2,3-d]pyridazin-8(7H)-one (RL-3) and the corresponding thione (RL-4).

In another embodiment of the invention, the application discloses a pharmaceutical composition comprising a therapeutically effective amount of a compound as disclosed above, and a pharmaceutically acceptable excipient. The application further discloses various embodiments of methods for the preparation of the disclosed compounds.

In another embodiment, there is provided a method for the treatment or amelioration of a cell proliferation disease comprising administration to a patient in need thereof a therapeutically effective amount of a compound or a pharmaceutical composition as disclosed above. In one aspect of this method, the therapeutically effective amount is effective to treat cancer. In another aspect, the cancer is associated with a kinase.

In another aspect of this method, the cancer is selected from the group consisting of colon carcinoma, pancreatic cancer, breast cancer, ovarian cancer, prostate cancer, squamous cell carcinoma, basal cell carcinoma, adenocarcinoma, renal cell carcinoma, cervical cancer, testicular tumor, lung carcinoma, small cell lung carcinoma, bladder carcinoma, melanoma, neuroblastoma, lymphoma and multiple myeloma.

In yet another aspect of this method, the compound or composition is administered via a route selected from the group consisting of oral, buccal, rectal, parenteral, intraperitoneal, intradermal, transdermal and intracheal.

Also included in the above embodiments, aspects and variations are the disclosed compounds formulated as salts of amino acids such as arginate and the like, gluconate, and galacturonate. Some of the compounds of the invention may form inner salts or Zwitterions. Certain of the compounds of the present invention can exist in unsolvated forms as well as solvated forms, including hydrated forms, and are intended to be within the scope of the present invention. Certain of the above compounds may also exist in one or more solid or crystalline phases or polymorphs, the variable biological activities of such polymorphs or mixtures of such polymorphs are also included in the scope of this invention. Also provided are pharmaceutical compositions comprising pharmaceutically acceptable excipients and a therapeutically effective amount of at least one compound of this invention.

Pharmaceutical compositions of the compounds of this invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration but may also be used for oral administration.

Excipients, such as polyvinylpyrrolidinone, gelatin, hydroxycellulose, acacia, polyethylene glycol, mannitol, sodium chloride, or sodium citrate, may also be added. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols or water. Solid carriers include starch, lactose, calcium sulfate, dihydrate, terra alba, magnesium stearate or stearic acid, talc, pectin, acacia, agar or gelatin.

The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing, and filling for hard gelatin capsule forms. When a liquid carrier is used, the preparation will be in the form of a syrup, elixir, emulsion, or an aqueous or non-aqueous suspension. Such a liquid formulation may be administered directly p.o. or filled into a soft gelatin capsule. Suitable formulations for each of these methods of administration may be found in, for example, *Remington: The Science and Practice of Pharmacy*, A. Gennaro, ed., 20th edition, Lippincott, Williams & Wilkins, Philadelphia, Pa.

In one variation, there is provided the above compound, or a pharmaceutically acceptable salt thereof, optionally in the form of a single stereoisomer or mixture of stereoisomers thereof.

In addition to the exemplary embodiments, aspects and variations described above, further embodiments, aspects and variations will become apparent by reference to the drawings and figures and by examination of the following descriptions.

DETAILED DESCRIPTION OF THE INVENTION

Description Of The Figures

FIG. 1 depicts representative results of biological screening of RL-1 using the National Cancer Institute (NCI) in single point dosing at 10 μM. The Growth Percent is given in tabular form. The graph shows the difference between the Growth Percent of each individual cell line and the Mean Growth Percent across all cell lines and is a depiction of specificity of RL-1.

FIG. 2 depicts representative results of biological screening of RL-2 using the NCI in single point dosing at 10 μM. The Growth Percent is given in tabular form. The graph shows the difference between the Growth Percent of each individual cell line and the Mean Growth Percent across all cell lines and is a depiction of specificity of RL-2.

FIG. 3 depicts representative results of biological screening of RL-3 using the NCI in single point dosing at 10 μM. The Growth Percent is given in tabular form. The graph shows the difference between the Growth Percent of each individual cell line and the Mean Growth Percent across all cell lines and is a depiction of specificity of RL-3.

FIG. 4 depicts representative results of biological screening of RL-4 using the NCI in single point dosing at 10 μM. The Growth Percent is given in tabular form. The graph shows the difference between the Growth Percent of each individual cell line and the Mean Growth Percent across all cell lines and is a depiction of specificity of RL-4.

FIG. 5 depicts representative results of biological screening of RL-4 using the NCI in five point dosing at $10^{-8}$ M, $10^{-7}$ M, $10^{-6}$ M, $10^{-5}$ M and $10^{-4}$ M. The tables show the raw data (mean optical densities), and the Percent Growth, GI50, TGI and LC50.

FIG. 6 depicts representative results of biological screening of RL-4 using the NCI in five point dosing at $10^{-8}$ M, $10^{-7}$ M, $10^{-6}$ M, $10^{-5}$ M and $10^{-4}$ M. The graphs show the Growth Percent as a function of the dosing concentration of RL-4. Each graph depicts the results for the cell lines that are within a particular panel, i.e., type of cancer.

FIG. 7 depicts representative results of biological screening of RL-4 using the NCI in five point dosing at $10^{-8}$ M, $10^{-7}$ M, $10^{-6}$ M, $10^{-5}$ M and $10^{-4}$ M. The tables present GI50, TGI and LC50 for each of 60 cell lines screened. Mean, Delta and Range are given across all cell lines for the three parameters GI50, TGI and LC50. The Mean graphs for each parameter show the deviation of the value for each cell line from the mean across all cell lines, which is an indication of specificity.

FIG. 8 depicts the results of the analysis using the MCF-7 and MCF-shWisp Models.

FIG. 9 depicts the potency results using the 2 epithelial cell lines Colo-205 and MCF-7.

FIG. 10 depicts the Cell Proliferation Assay results using DLD-1TR21 and DLD-Snail models.

FIG. 11 depicts the Cell Proliferation Assay results using DLD-1TR21 and DLD-Snail models.

FIG. 12 depicts the Ortep drawings of X-Ray crystallographic structures of RL-3 and RL-4.

DEFINITIONS

Unless specifically noted otherwise herein, the definitions of the terms used are standard definitions used in the art of organic synthesis and pharmaceutical sciences. Exemplary embodiments, aspects and variations are illustrative in the figures and drawings, and it is intended that the embodiments, aspects and variations, and the figures and drawings disclosed herein are to be considered illustrative and not limiting.

An "alkyl" group is a straight, branched, saturated or unsaturated, aliphatic group having a chain of carbon atoms, optionally with oxygen, nitrogen or sulfur atoms inserted between the carbon atoms in the chain or as indicated. A $(C_1-C_{20})$alkyl, for example, includes alkyl groups that have a chain of between 1 and 20 carbon atoms, and include, for example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, penta-1,4-dienyl, hexa-1,3-dienyl, hexa-1,3,5-trienyl, and the like. A $(C_1-C_6)$alkyl, for example, includes alkyl groups that have a chain of between 1 and 6 carbon atoms, and include, for example, the groups methyl, ethyl, propyl, isopropyl, vinyl, allyl, 1-propenyl, isopropenyl, ethynyl, 1-propynyl, 2-propynyl, butyl, 1,3-butadienyl, pentyl, hexyl etc . . . . An alkyl group may also be represented, for example, as a $—(CR^1R^2)_m—$ group where $R^1$ and $R^2$ are independently hydrogen or are independently absent, and for example, m is 1 to 8, and such representation is also intended to cover both saturated and unsaturated alkyl groups.

An alkyl as noted with another group such as an aryl group, represented as "arylalkyl" for example, is intended to be a straight, branched, saturated or unsaturated aliphatic divalent group with the number of atoms indicated in the alkyl group (as in $(C_1-C_{20})$alkyl, for example) and/or aryl group (as in $(C_5-C_{14})$aryl, for example) or when no atoms are indicated means a bond between the aryl and the alkyl group. Nonexclusive examples of such group include benzyl, phenethyl and the like.

An "alkylene" group is a straight, branched, saturated or unsaturated aliphatic divalent group with the number of atoms indicated in the alkyl group; for example, a $—(C_1-C_3)$ alkylene- or $—(C_1-C_3)$alkylenyl-.

A "cyclyl" such as a monocyclyl or polycyclyl group includes monocyclic, or linearly fused, angularly fused or bridged polycycloalkyl, or combinations thereof. Such cyclyl group is intended to include the heterocyclyl analogs. A cyclyl group may be saturated, partially saturated or aromatic.

"Halogen" or "halo" means fluorine, chlorine, bromine or iodine.

A "heterocyclyl" or "heterocycle" is a cycloalkyl wherein one or more of the atoms forming the ring is a heteroatom that is a N, O, or S, Non-exclusive examples of heterocyclyl include piperidyl, 4-morpholyl, 4-piperazinyl, pyrrolidinyl, 1,4-diazaperhydroepinyl, 1,3-dioxanyl, and the like.

"Pharmaceutically acceptable salts" means salt compositions that is generally considered to have the desired pharmacological activity, is considered to be safe, non-toxic and is acceptable for veterinary and human pharmaceutical applications. Such salts include acid addition salts formed with inorganic acids such as hydrochloric acid, hydrobromic acid, sulfuric acid, phosphoric acid, and the like; or with organic acids such as acetic acid, propionic acid, hexanoic acid, malonic acid, succinic acid, malic acid, citric acid, gluconic acid, salicylic acid and the like.

"Therapeutically effective amount" means a drug amount that elicits any of the biological effects listed in the specification.

"Substituted or unsubstituted" or "optionally substituted" means that a group such as, for example, alkyl, aryl, heterocyclyl, ($C_1$-$C_8$)cycloalkyl, heterocyclyl($C_1$-$C_8$)alkyl, aryl ($C_1$-$C_8$)alkyl, heteroaryl, heteroaryl($C_1$-$C_8$)alkyl, and the like, unless specifically noted otherwise, may be unsubstituted or, may substituted by 1, 2 or 3 substituents selected from the group such as halo (F, Cl, Br, I), nitro, trifluoromethyl, trifluoromethoxy, methoxy, carboxy, —$NH_2$, —OH, —SH, —$NHCH_3$, —$N(CH_3)_2$, —SMe, —CN and the like.

EXPERIMENTAL

Synthesis of Rilyazine Derivatives

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Suitable protective groups for amino, hydroxy, and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989.

Initially, four compounds were synthesized (Table 1): 6-cyclohexyl-8-(pyridin-2-yl)pyrido[2,3-d]pyridazin-5 (6H)-one (RL-1) and the corresponding thione (RL-2) as well as 7-cyclohexyl-5-(pyridin-2-yl)pyrido[2,3-d]pyridazin-8 (7H)-one (RL-3) and the corresponding thione (RL-4). There are two regio-isomeric pairs (compounds 1 and 3; and compounds 2 and 4) in this series differing only in the position of the nitrogen in the pyridyl portion of the pyrido-pyridazine core.

Single point 60 cell line testing at 10 μM indicated that RL-1, RL-2 and RL-3 showed little to no appreciable antiproliferative effects against cancer, FIGS. 1-3. None of the compounds RL-1, RL-2 and RL-3 met the criterion for 50% growth inhibition at the μM tested, that is, GI50>10 μM, Table 1.

Single point 60 cell line testing at 10 μM indicated that RL-4 has anti-proliferative effects against cancer. Of the 60 cell lines tested, 22 showed growth inhibition ≥50% at the 10 μM RL-4 dosage level, GI50≤10 μM, Table 1 and FIG. 4.

Single point 60 cell line testing at 10 μM also indicated that RL-4 is relatively non-toxic. At the 10 μM RL-4 dosage level, none of the 60 cell lines had a growth percent less than 0%, FIG. 4, which would be an indication of cell death, from which it follows that the LC50 (concentration at which 50% of cells are killed) >10 μM, Table 1.

TABLE 1

Rilyazines RL-1 to RL-4

| Name | Structure | NCI Results, single point, 10 μM |
|---|---|---|
| RL-1 | (structure) | GI50 > 10 μM |
| RL-2 | (structure) | GI50 > 10 μM |
| RL-3 | (structure) | GI50 > 10 μM |

TABLE 1-continued

Rilyazines RL-1 to RL-4

| Name | Structure | NCI Results, single point, 10 μM |
|---|---|---|
| RL-4 | 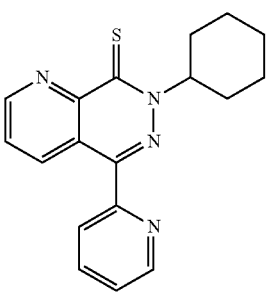 | GI50 ≤ 10 μM for 22 of 60 cell lines<br>LC50 > 10 μM for all 60 cell lines tested |

Each of the Rilyazines RL-1 through RL-4 may be synthesized according to the procedure of Scheme 1. Furo[3,4-b]pyridine-5,7-dione is reacted with ethanol in the presence of an acid, such as $H_2SO_4$, resulting in diethyl pyridine-2,3-dicarboxylate (1), which is then reacted with freshly-prepared pyridin-2-yl lithium to afford ethyl 2-picolinoylnicotinate (2) and ethyl 3-picolinoylpicolinate (3). Separation of the isomers (2) and (3) by chromatography and their reactions with cyclohexylhdrazine hydrochloride affords the ketone-Rilyazines RL-1 and RL-3, which may then be converted to the corresponding thione-Rilyazines RL-2 and RL-4 by reaction with Lawesson reagent.

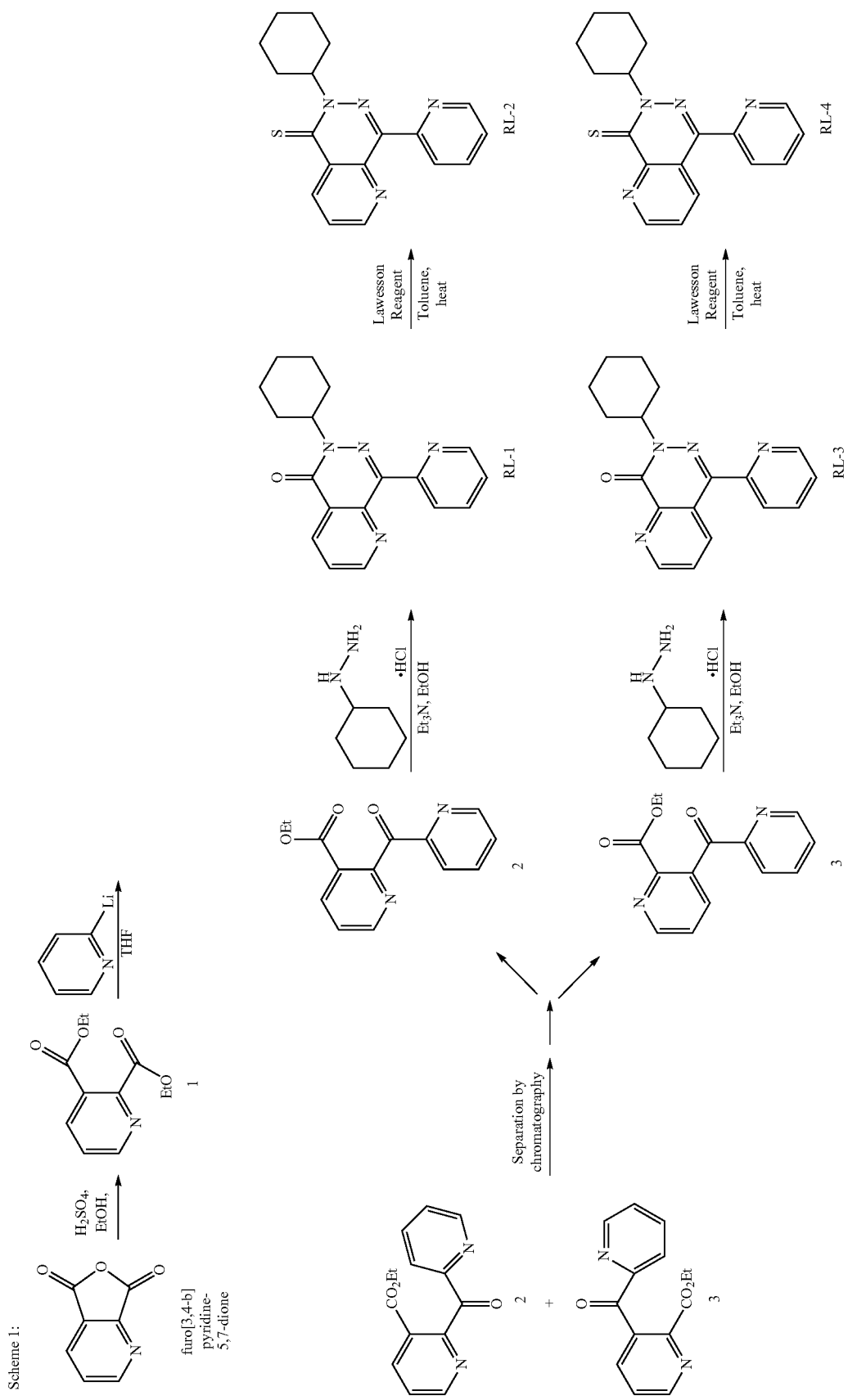
Scheme 1:

RL-1 through RL-4 were screened by the NCI in single point dosing at 10 μM. RL-1 through RL-3 showed little or only marginal activity; however, in general, RL-4 showed cell growth inhibition across the screened cell lines with no associated toxicity. RL-1, RL-2, RL-3 and RL-4 results are shown in FIGS. 1-4. The apparent range of growth inhibition in various cancer cell lines is observed. Although the mechanism of action has not been fully ascertained, it is evident that certain cell lines are more susceptible to growth inhibition from RL-4.

Growth percent of cancer cells exposed to RL-4: RL-4 shows significant growth inhibition in cancer cell lines. No Toxicity is observed. (NCI, single point study).

RL-4 was screened by the NCI in five point dosing at $10^{-8}$ M, $10^{-7}$ M, $10^{-6}$ M, $10^{-5}$ M and $10^{-4}$ M. RL-4 results for the five point dosing are shown in FIGS. 5-7.

RL-4 showed significant growth inhibition across all 60 cell lines screened at some level of dosage tested. The Mean GI50 for all 60 cell lines, where GI50 is the concentration of RL-4 at which the Percent Growth Inhibition is 50%, is $2 \times 10^{-5}$ M.

Because the RL class of compounds provides multiple sites $R^1$, $R^2$ and $R^3$ for variations in the substituents present on the (pyridinyl)pyrido-pyridazinone or (pyridinyl)pyrido-pyridazinthione backbone, it provides a unique opportunity for fine-tuning selectivity, improving SAR, SPR and other relevant medicinal chemistry parameters. The class of compounds RL-D, of which RL-4 is a member, was prioritized for additional development, targeting three additional analogs in efforts to gain more perspective in this series. Related compounds in the inactive or low activity series, RL-A, RL-B, and RL-C, were also synthesized. Compounds with various substitution of the pyridazine were prepared with the substituents ethyl, benzyl and pyridin-2yl-methyl, depicted in the structures below.

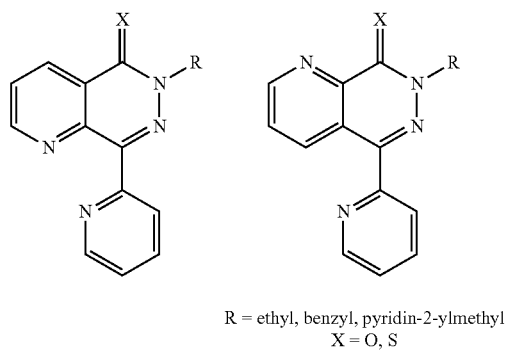

R = ethyl, benzyl, pyridin-2-ylmethyl
X = O, S

Rilyazines with substitutents other than the cyclohexyl may be prepared similarly to the reactions shown in Scheme 1, provided the substituted hydrazine can be prepared or obtained from commercial sources.

Alternate methods of synthesis of the Rilyazines were designed to improve overall yield and improve upon stereospecificity, and to eliminate the requirement for availability of the appropriately-substituted hydrazine used in Scheme 1. These alternate syntheses were used for the synthesis of the Rilyazines RL-6 through RL-17, and may be adapted to the synthesis of the Rilyazines RL-1 through RL-4 or other Rilyazine derivatives.

One such alternate procedure begins with the initial steps shown in Synthetic Scheme 2. Synthetic Scheme 2 begins with the conversion of 2,3-pyridinedicarboxylic acid to the 2,3-pyridinedicarboxylic anhydride (furo[3,4-b]pyridine-5,7-dione) by heating with acetic anhydride. Although 2,3-pyridinedicarboxylic anhydride is commercially available, it was uniformly found to be contaminated with the 2,3-pyridinedicarboxylic acid hydrolysis product, and, if purchased as the anhydride, was always subjected to the same procedure for conversion to the anhydride. The 2,3-pyridinedicarboxylic anhydride is reacted with a Grignard reagent, 2-pyridyl magnesium bromide, to form the mixed isomeric 2-picolinoylnicotinic and 3-picolinoylpicolinic acids, 4 and 5. The major (~3:1) product of the reaction of 2,3-pyridinedicarboxylic anhydride with 2-pyridyl magnesium bromide is the 2-picolinoylnicotinic acid 4. The isomers 4 and 5 can be separated by reverse-phase flash chromatography. The acids 4 and 5 may each be separately converted to their corresponding methyl esters, methyl 2-picolinoylnicotinate 6 and methyl 3-picolinoylpicolinate 7. Only the methyl 2-picolinoylnicotinate 6 was prepared by reaction of the acid 4 according to the method of Synthetic Scheme 2. An alternate, regiospecific method of synthesis of methyl 3-picolinoylpicolinate 7 is detailed in Synthetic Scheme 6.

Scheme 2:

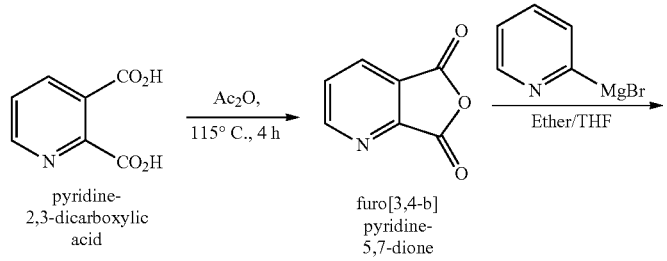

pyridine-
2,3-dicarboxylic
acid furo[3,4-b]
pyridine-
5,7-dione

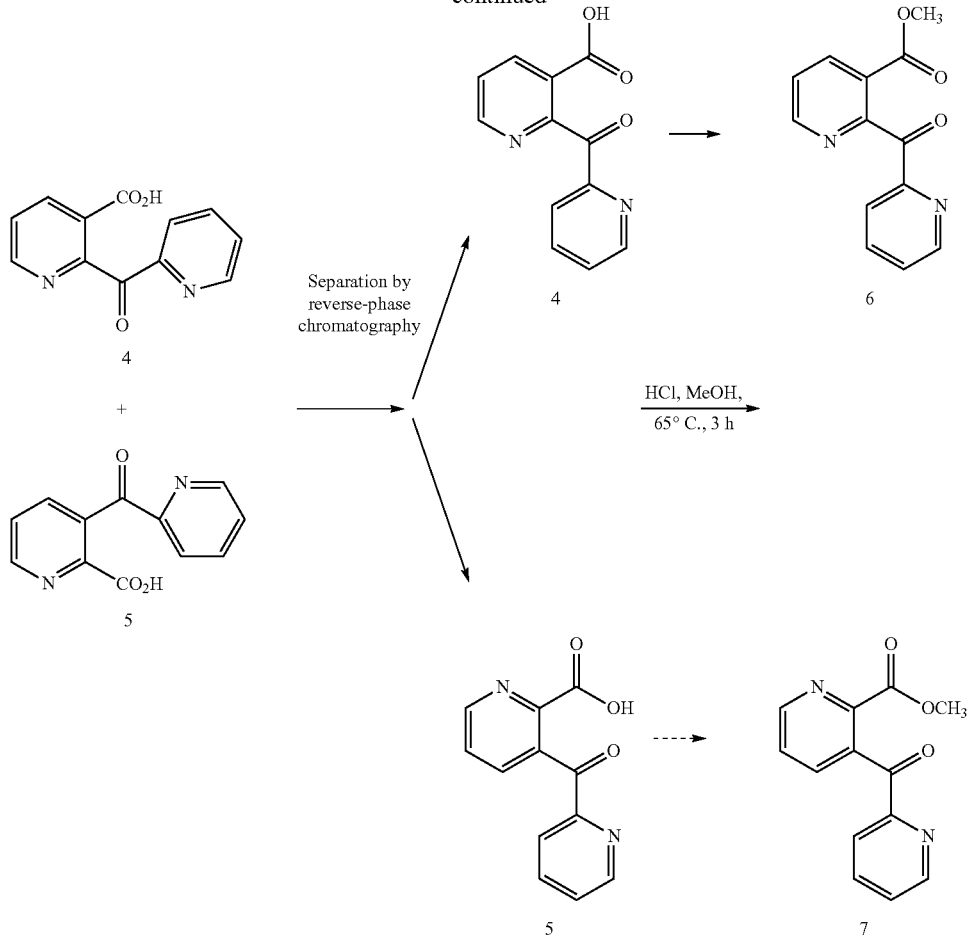

The reaction of either the methyl 2-picolinoylnicotinate 6 or methyl 3-picolinoylpicolinate 7 with an R²-substituted hydrazine provides a one-step route to the corresponding ketone-Rilyazine, as illustrated in Synthetic Scheme 3 for the synthesis of 6-benzyl-8-(pyridin-2-yl)pyrido[2,3-d]pyridazin-5(6H)-one, RL-10. The ketone-Rilyazine can be further converted to the thione-Rilyazine with Lawesson Reagent, Synthetic Scheme 3, shown for conversion of the benzyl derivative RL-10 conversion to RL-11.

Scheme 3:

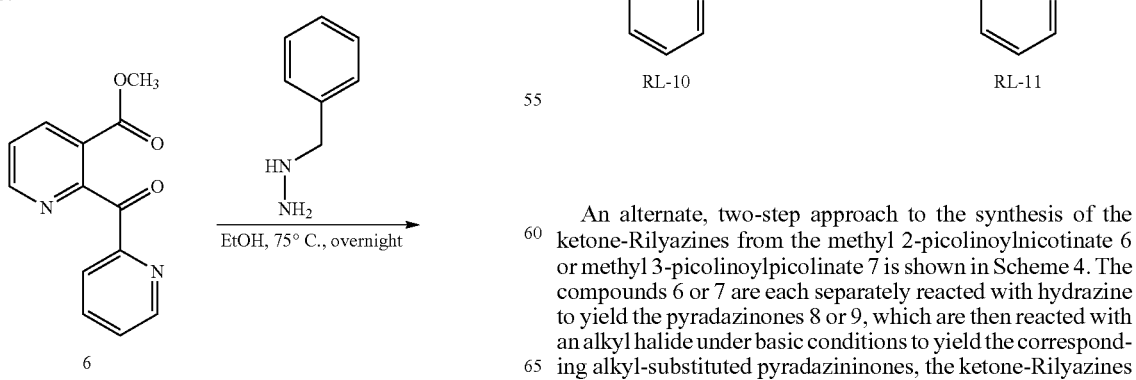

An alternate, two-step approach to the synthesis of the ketone-Rilyazines from the methyl 2-picolinoylnicotinate 6 or methyl 3-picolinoylpicolinate 7 is shown in Scheme 4. The compounds 6 or 7 are each separately reacted with hydrazine to yield the pyradazinones 8 or 9, which are then reacted with an alkyl halide under basic conditions to yield the corresponding alkyl-substituted pyradazininones, the ketone-Rilyazines 10 or 11. Further conversion can be effected by reaction with Lawesson Reagent to yield the thione-Rilyazines 12 or 13.

Scheme 4:

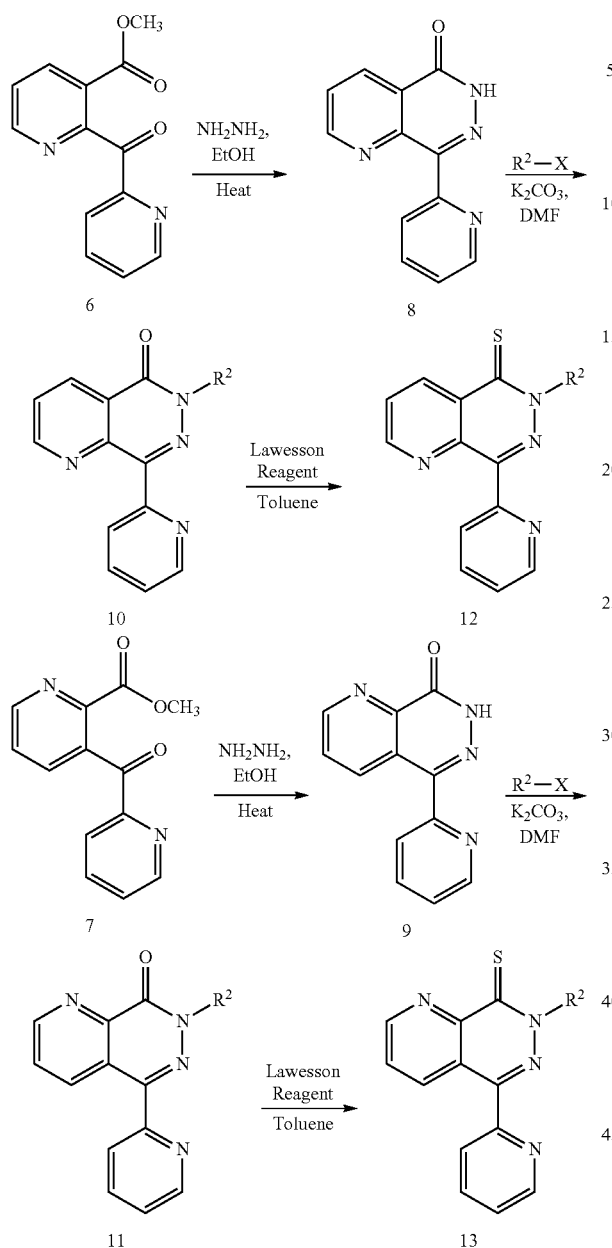

Scheme 5:

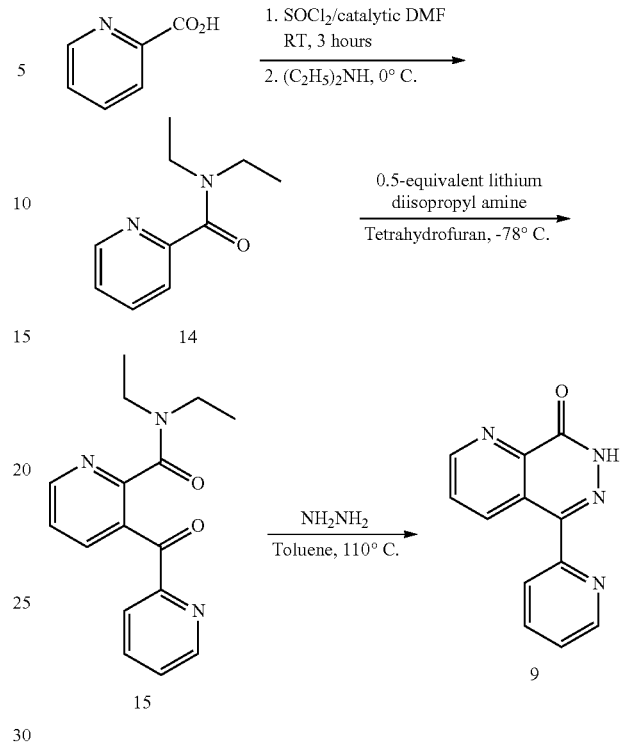

An alternate, regiospecific synthesis of the unsubstituted pyradazinone 9 is shown in Scheme 5. Picolinic acid is converted to picolinoyl chloride by reaction with thionyl chloride. Without isolation, the so-formed picolinoyl chloride is then condensed with diethylamine to form N,N-diethylpicolinamide 14. Directed ortho-metallation of N,N-diethylpicolinamide 14 with 0.5 equivalent lithium diisopropyl amine and condensation of the resulting metallated compound with the remaining 0.5 equivalent of unmetallated N,N-diethylpicolinamide 14 results in the formation of N,N-diethyl-3-picolinoylpicolinamide, 15. Reaction of 15 with hydrazine yields the pyridazinone 9.

The pyradazinone 9 can be converted to the various ketone-Rilyazines 11, and then to the corresponding thione-Rilyazines 13, similarly to the methods shown in Scheme 4 for conversion of compound 9 to 11 to 13.

Synthetic Scheme 6 is yet another method of regiospecific synthesis of the methyl 3-picolinoylpicolinate 7 and 5-(pyridin-2-yl)pyrido[2,3-d]pyridazin-8(7H)-one 9. N,N-diethylpicolinamide 14, prepared as in Synthetic Scheme 5, is reacted with 1 equiv of sec-butyl lithium, and, without isolation of the lithiated intermediate, a second equivalent of N,N-diethylpicolinamide 14 is added to the reaction mixture, resulting in the condensation reaction yielding lithium 3-picolinoylpicolinate 16. Lithium 3-picolinoylpicolinate 16 is reacted with methanol to yield the methyl ester, methyl 3-picolinoylpicolinate 7, which is then reacted with hydrazine to yield 5-(pyridin-2-yl)pyrido[2,3-d]pyridazin-8(7H)-one 9. The pyridazinone 9 can be converted to the various ketone-Rilyazines 11, and then to the corresponding thione-Rilyazines 13 similarly to the methods shown in Scheme 4.

Scheme 6:

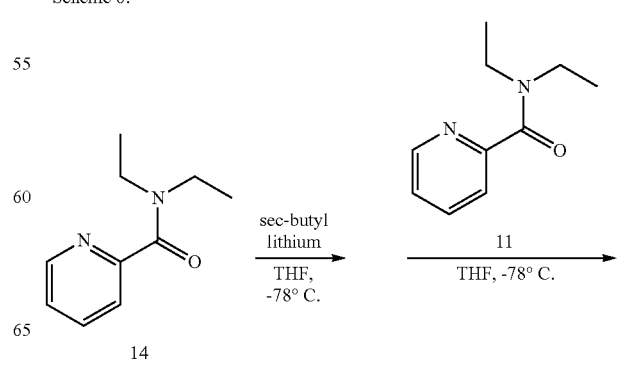

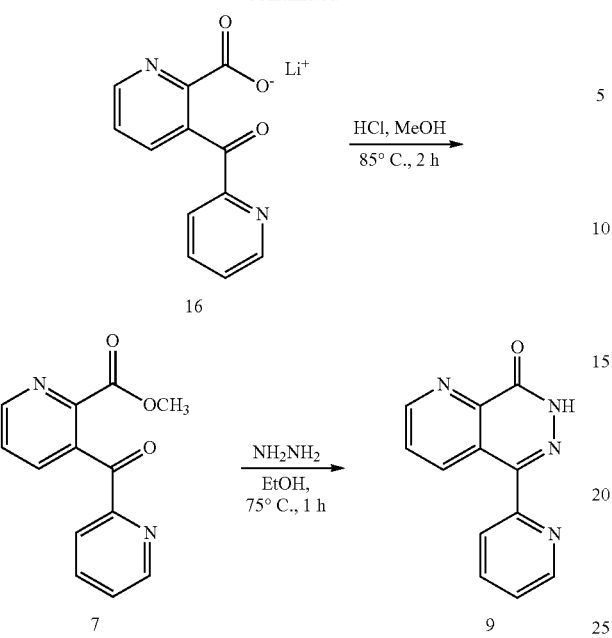
All of the Rilyazine analogs RL-1 through RL-4 and RL-6 through RL-17, as shown, have been prepared.
RL-1
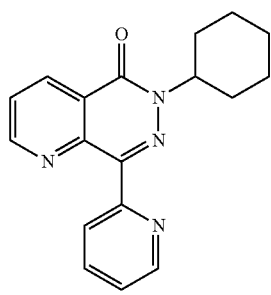 [SMILES: O=c1c2cccnc2c(-c2ccccn2)nn1C1CCCCC1]
RL-2
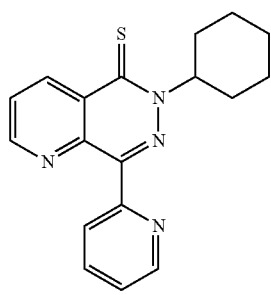 [SMILES: S=c1c2cccnc2c(-c2ccccn2)nn1C1CCCCC1]
RL-3
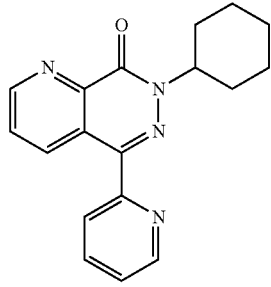 [SMILES: O=c1c2ncccc2c(-c2ccccn2)nn1C1CCCCC1]
RL-4
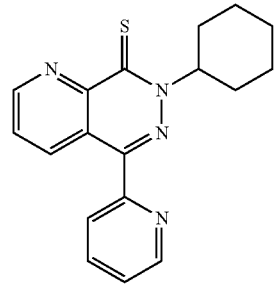 [SMILES: S=c1c2ncccc2c(-c2ccccn2)nn1C1CCCCC1]
RL-6
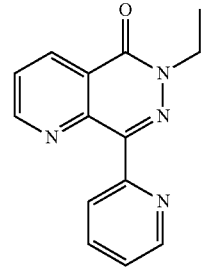
RL-7
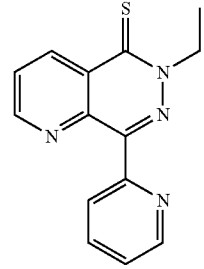
RL-8
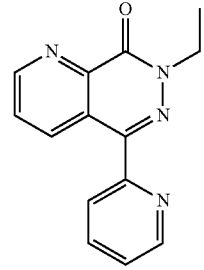
RL-9
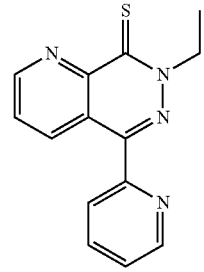

RL-10
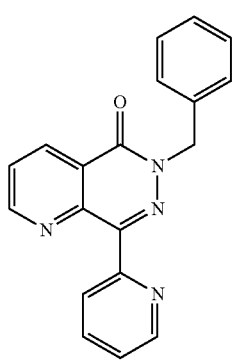
RL-11
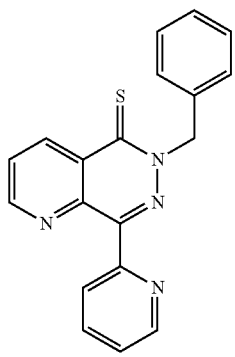
RL-12
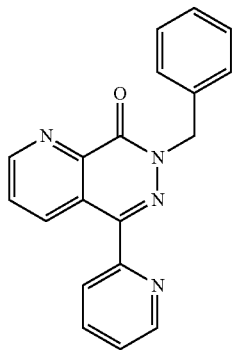
RL-13
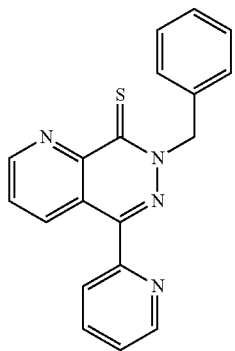
RL-14
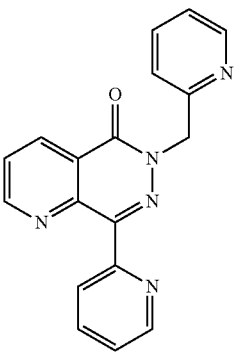
RL-15
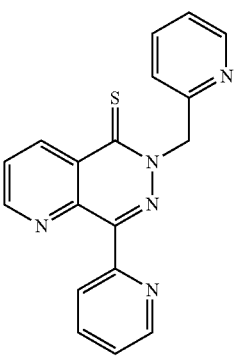
RL-16
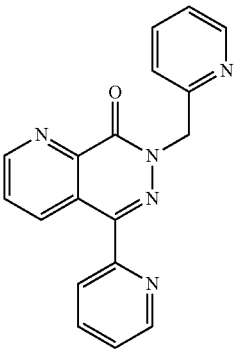
RL-17
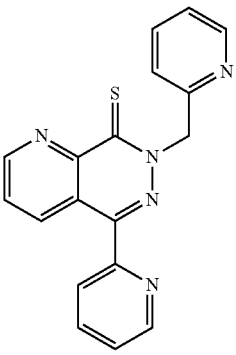
The structures for RL-3 and RL-4 have been confirmed by X-Ray crystallography. The Ortep representations were as expected and are shown in FIG. 12.
Biological evaluation of the compounds RL-1, RL-2, RL-3, and RL-4 were performed.
Based on the favorable, initial studies of 4 compounds RL-1, RL-2, RL-3 and RL-4, in the Rilyazine series as potential leads for anti-cancer compounds with reduced toxicity profiles, 12 new compounds RL-6 through RL-17 were synthesized and characterized.

The compound of the present application may be prepared as disclosed herein using standard methods known in the art. In one embodiment, the compound of the formula A is contacted with a hydrazine ($R^7$—$NH_2NH_2$) or hydrazine hydrochloride under condition sufficient for a sufficient period of time to form the compound of the oxo-Rilyazine of the formula B. In one variation, the conversion is performed in an organic solvent and a base, such as an alcohol and an amine base. The oxo-Rilyazine of the formula B may be converted to the corresponding thio-Rilyazine C using a thionylation agent, such as Lawesson's Reagent in an organic solvent, such as toluene or xylenes. The thionylation reaction may be performed at an elevated temperature, such as about 100° C. to 120° C. or at refluxing temperatures for a sufficient period of time to form compound C.

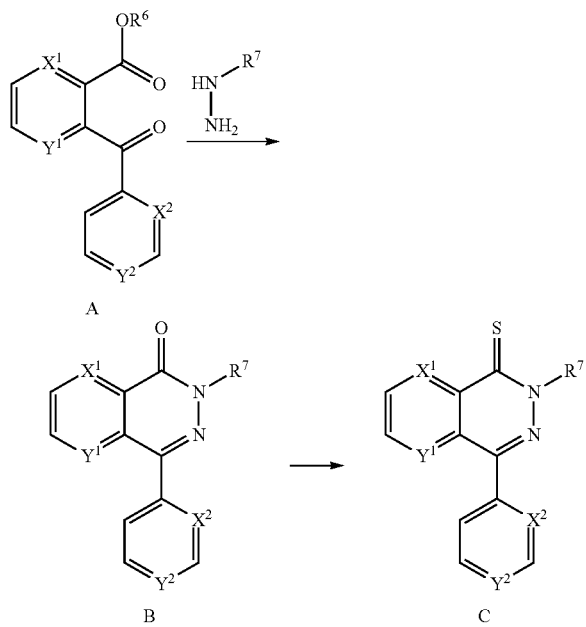

In one aspect of the above compounds A, B and C, each $X^1$ and $X^2$ is independently C or N, and each $Y^1$ and $Y^2$ is independently C or N. In another aspect of the above compounds A, B and C, $X^1$ is N, and $X^2$ and $Y^1$ and $Y^2$ are C. In one aspect of the above compounds A, B and C, $X^1$ and $X^2$ are N and $Y^1$ and $Y^2$ are C.

EXPERIMENTAL

General: All reagents were purchased from commercial suppliers and used as supplied unless stated otherwise. Reactions were carried out in air unless stated otherwise. 400 MHz $^1$H NMR spectra were obtained on a JEOL AS 400 spectrometer. Low-resolution mass spectra (LRMS) were obtained on a JEOL JMS-T100LC DART/AccuTOF and liquid chromatography/mass spectrometer (LCMS) was performed on an Agilent 6120 Quadrupole LCMS system.

X-Ray Crystallography: A colorless plate crystal of as-supplied RL-3 with dimensions 0.22×0.20×0.06 mm was mounted on a Nylon loop using very small amount of paratone oil. Yellow needle crystals of RL-4 were prepared by evaporation of a methylene chloride solution of the compound. A crystal of RL-4 with dimensions 0.34×013×0.10 mm was mounted on a Nylon loop using very small amount of paratone oil. Data for each compound were collected using a Bruker CCD (charge coupled device) based diffractometer equipped with an Oxford Cryostream low-temperature apparatus operating at 173 K. Data were measured using omega and phi scans of 1.0° per frame for 30 s. The total number of images was based on results from the program COSMO where redundancy was expected to be 4.0 and completeness to 100% out to 0.83 A. Cell parameters were retrieved using CELL_NOW program which is part of APEX II software and refined using SAINT on all observed reflections. Data reduction was performed using the SAINT software which corrects for Lp. Scaling and absorption corrections were applied using TWINABS multi-scan technique to separate out the two twin components and allow the major component to be provided for solution and refinement. Structures were solved using standard techniques.

Structures of RL-3 and RL-4 are shown in FIG. 12.

In one variation, the specific functionalized compounds RL-1 to RL-4 of the application may be synthesized by the steps outlined in Scheme 1.

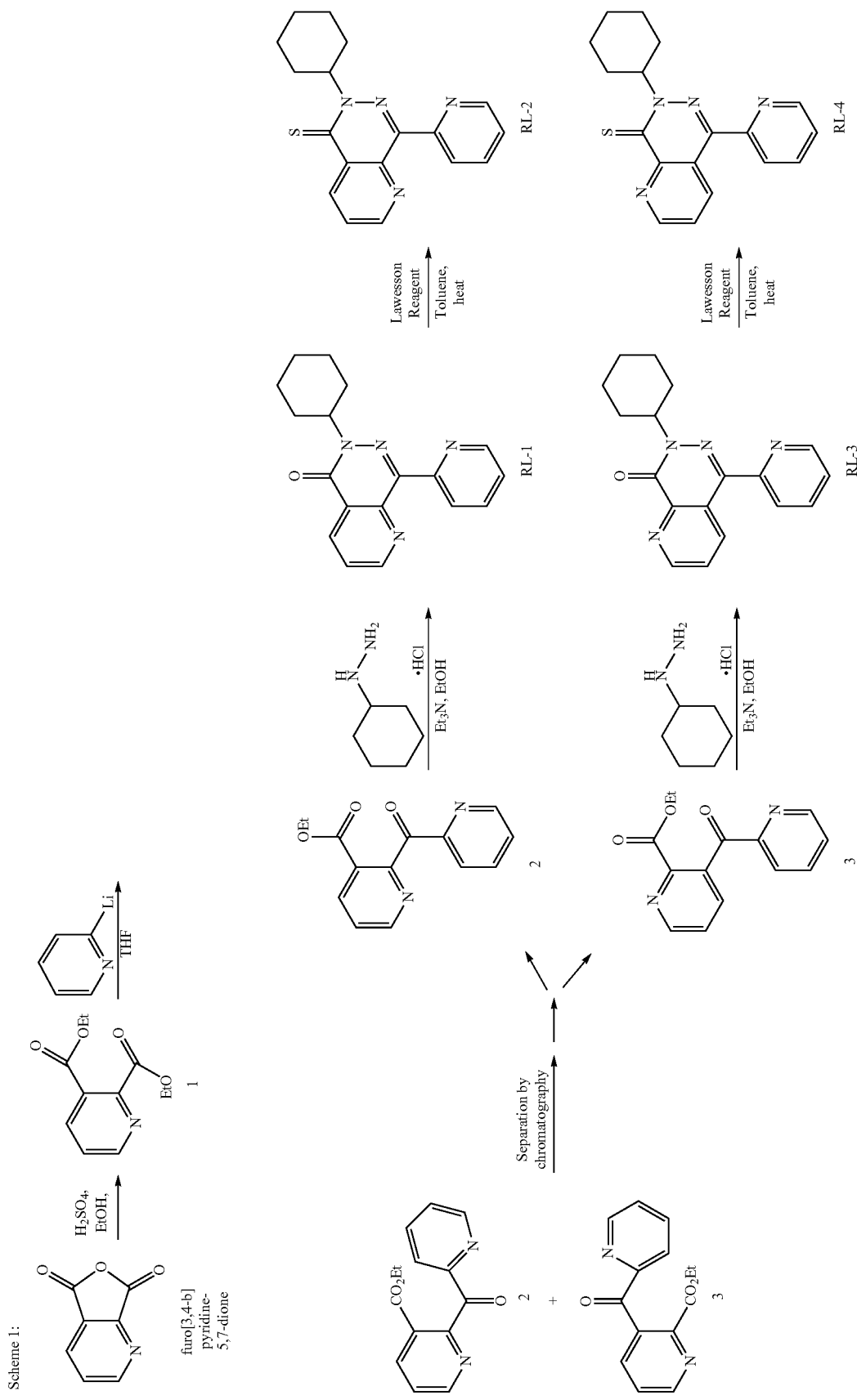
Scheme 1:

Synthetic Procedure

Diethyl pyridine-2,3-dicarboxylate (2): Adapted from the *Journal of Organic Chemistry*, 74 (17), 6863, 2009.

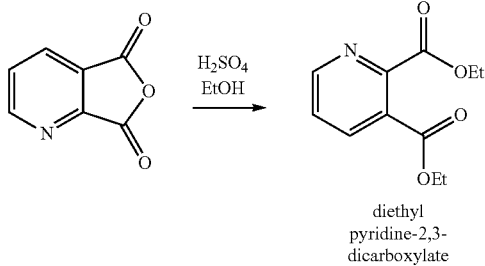 [SMILES: O=C1OC(=O)c2ncccc21 ; CCOC(=O)c1cccnc1C(=O)OCC]

diethyl pyridine-2,3-dicarboxylate 2,3-Pyridinedicarboxylic anhydride (10.0 g) was dissolved in ethanol (113 mL) and 98% sulfuric acid 11.3 mL) was added. The mixture was heated to reflux for 16 hours, then cooled to room temperature. Saturated aqueous ammonium hydroxide (30 mL) was added, followed by sufficient water to dissolve the precipitate. The ethanol was removed in vacuo and the aqueous layer extracted with ethyl acetate (3×75 mL). The combined organic fraction was washed with brine, dried over magnesium sulfate and concentrated to afford diethyl pyridine-2,3-dicarboxylate (11.39 g). $^1$H-NMR (400 MHz, CDCl$_3$) δ 8.74 (dd, 1H), 8.17 (dd, 1H), 7.46 (dd, 1H), 4.45 (q, 2H), 4.37 (q, 2H), 1.40 (t, 3H), 1.36 (t, 3H).

Ethyl 2-picolinoylnicotinate (2) and Ethyl 3-picolinoylpicolinate (3)

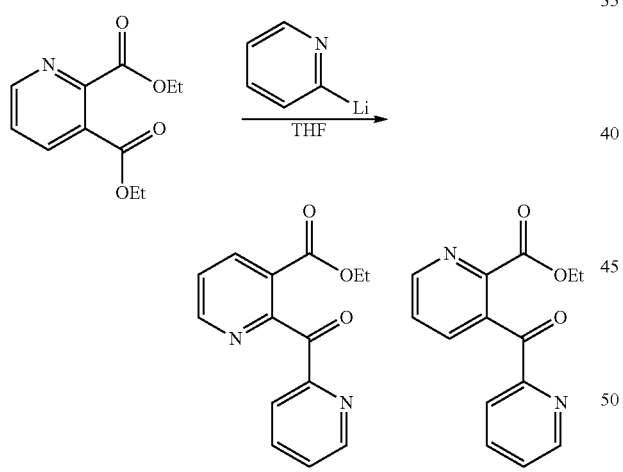

To a flame-dried, 100 mL flask was added 2-bromopyridine (0.24 mL) and anhydrous tetrahydrofuran (14.9 mL). This solution was cooled to −78° C. in a dry ice/acetone bath and a 2.0 M solution of n-butyl lithium (1.34 mL) was added drop wise. The resulting orange solution was stirred for 30 minutes at −78° C. A solution of diethyl pyridine-2,3-dicarboxylate (0.50 g) in anhydrous tetrahydrofuran was cooled to −78° C. and added to the reaction via cannula. The reaction was maintained at −78° C. for 1 hour, then quenched by the addition of water (20 mL) and a saturated solution of ammonium chloride (20 mL). The reaction was warmed to room temperature and the layers separated.

The aqueous was extracted with ethyl acetate (3×30 mL), and the combined organic layer washed with brine, dried over magnesium sulfate, filtered and concentrated. The residue was purified via chromatography on silica gel (1$^{st}$ column: 0 to 3% methanol in dichloromethane, 2$^{nd}$ column: 0 to 100% ethyl acetate in hexanes) to afford ethyl 2-picolinoylnicotinate (0.83 g) and ethyl 3-picolinoylpicolinate (0.76 g).

Ethyl 2-picolinoylnicotinate (2): $^1$H-NMR (400 MHz, CDCl$_3$) δ 8.81 (dd, 1H), 8.55 (ddd, 1H), 8.37 (dd, 1H), 8.31 (dt, 1H), 9.90 (td, 1H), 7.49 (dd, 1H), 7.43 (ddd, 1H), 4.12 (q, 2H), 1.06 (t, 3H).

Ethyl 3-picolinoylpicolinate (3): $^1$H-NMR (400 MHz, CDCl$_3$) δ 8.82 (dd, 1H), 8.52 (ddd, 1H), 8.26 (dt, 1H), 7.93-7.87 (m, 2H), 7.57 (d, 1H), 7.42 (ddd, 1H), 4.13 (q, 2H), 1.14 (t, 3H).

6-Cyclohexyl-8-(pyridin-2-yl) pyrido[2,3-d]pyridazin-5(6H)-one (RL-1)

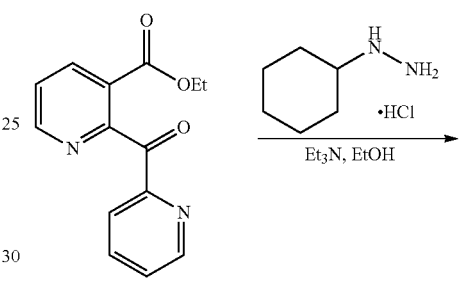

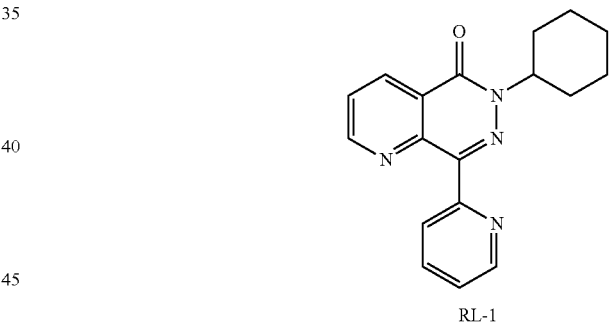

RL-1

To a solution of ethyl 2-picolinoyl nicotinate (0.35 g) in ethanol (13.7 mL) was added cyclohexylhydrazine hydrochloride (0.31 g) and triethylamine (0.26 mL). The reaction was heated at reflux for 24 then cooled to room temperature. The ethanol was removed in vacuo and the residue redissolved in dichloromethane (30 mL). The organic layer was washed with saturated sodium bicarbonate solution (20 mL) and this back-extracted with dichloromethane (2×20 mL). The combined organic layer was dried over magnesium sulfate, filtered and concentrated.

The residue was purified via chromatography on silica gel (0 to 4.5% methanol in dichloromethane) to afford 6-cyclohexyl-8-(pyridin-2-yl)pyrido[2,3-d]pyridazin-5(6H)-one (RL-1, 0.28 g). $^1$H-NMR (400 MHz, CDCl$_3$) δ 9.10 (dd, 1H), 8.83 (d, 1H), 8.77 (dd, 1H), 7.87 (td, 1H), 7.79 (d, 1H), 7.65

(dd, 1H), 7.41 (ddd, 1H), 5.11-4.98 (m, 1H), 1.98-1.84 (m, 6H), 1.71 (broad d, 1H), 1.56-1.41 (m, 2H), 1.31-1.16 (m, 1H). LRMS: 307.13 (M+H)+.

7-Cyclohexyl-5-(pyridin-2-yl)pyrido[2,3-d]pyridazin-8(7H)-one (RL-3)

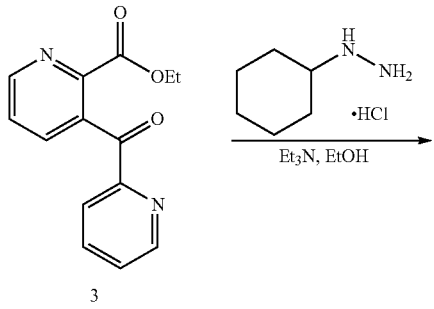

The isomer RL-3 was similarly prepared by reaction of ethyl 3-picolinoylpicolinate (3). 1H-NMR (400 MHz, CDCl3) δ 9.20 (dd, 1H), 9.10 (dd, 1H), 8.73-8.70 (m, 1H), 7.99 (dt, 1H), 7.88 (td, 1H), 7.69 (dd, 1H), 7.40 (ddd, 1H), 5.24-5.15 (m, 1H), 2.01-1.81 (m, 6H), 1.74 (broad d, 1H), 1.60-1.46 (m, 2H), 1.32-1.19 (m, 1H). LRMS: 307.13 (M+H)+.

6-Cyclohexyl-8-(pyridin-2-yl) pyrido[2,3-d]pyridazine-5(6H)-thione (RL-2)

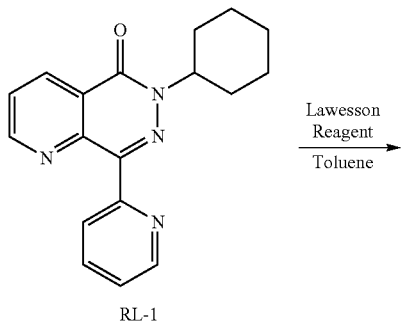

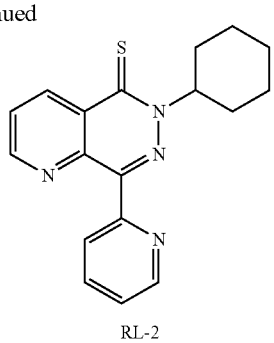

To a nitrogen flushed flask fitted with a reflux condenser was added 6-cyclohexyl-8-(pyridin-2-yl)pyrido[2,3-d]pyridazin-5(6H)-one (RL-1, 0.31 g) and 2,4-Bis(4-methoxyphenyl)-2,4-dithioxo-1,3,2,4-dithiadiphosphetane (Lawesson Reagent, 0.25 g). Anhydrous toluene (10.2 mL) was added and the reaction was heated to reflux for 3 hours, then cooled to room temperature.

The toluene was removed in vacuo and the residue purified via chromatography on silica gel (0 to 4% methanol in dichloromethane) to afford 6-cyclohexyl-8-(pyridin-2-yl)pyrido[2,3-d]pyridazine-5(6H)-thione (RL-2, 0.22 g.). 1H-NMR (400 MHz, CDCl3) δ 9.30 (dd, 1H), 9.09 (dd, 1H), 8.84 (ddd), 7.88 (td, 1H), 7.80 (dt, 1H), 7.66 (dd, 1H), 7.44 (ddd, 1H), 6.11-6.01 (m, 1H), 2.09 (broad d, 2H), 1.95-1.83 (m, 4H), 1.73 (broad d, 1H), 1.59-1.45 (m, 2H), 1.33-1.18 (m, 1H). LRMS: 323.10 (M+H)+.

7-cyclohexyl-5-(pyridin-2-yl)pyrido[2,3-d]pyridazine-8(7H)-thione (RL-4)

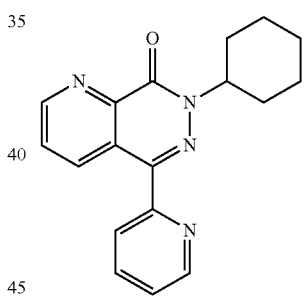

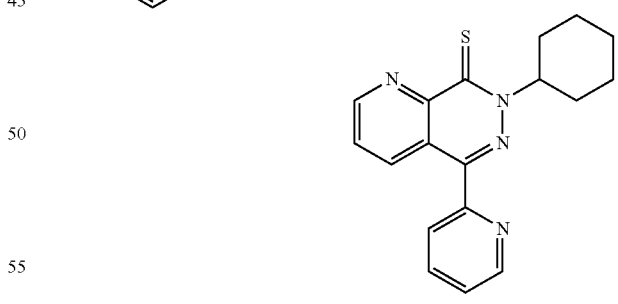

The other thione isomer (RL-4) was similarly prepared. 1H-NMR (400 MHz, CDCl3) δ 9.25 (dd, 1H), 9.21 (dd, 1H), 8.75 (ddd, 1H), 8.03 (dt, 1H), 7.93 (td, 1H), 7.71 (dd, 1H), 7.45 (ddd, 1H), 6.23-6.13 (m, 1H), 2.15 (broad d, 2H), 1.96-1.81 (m, 4H), 1.76 (broad d, 1H), 1.62-1.47 (m, 2H), 1.35-1.21 (m, 1H). LRMS: 323.11 (M+H)+.

In another variation, the intermediates methyl 2-picolinoylnicotinate 6 or methyl 3-picolinoylpicolinate 7 may be synthesized by the steps outlined in Scheme 2 for subsequent conversion to Rilyazines.

Scheme 2:

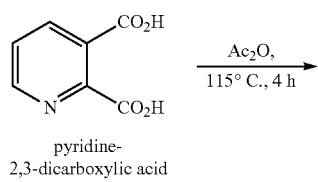

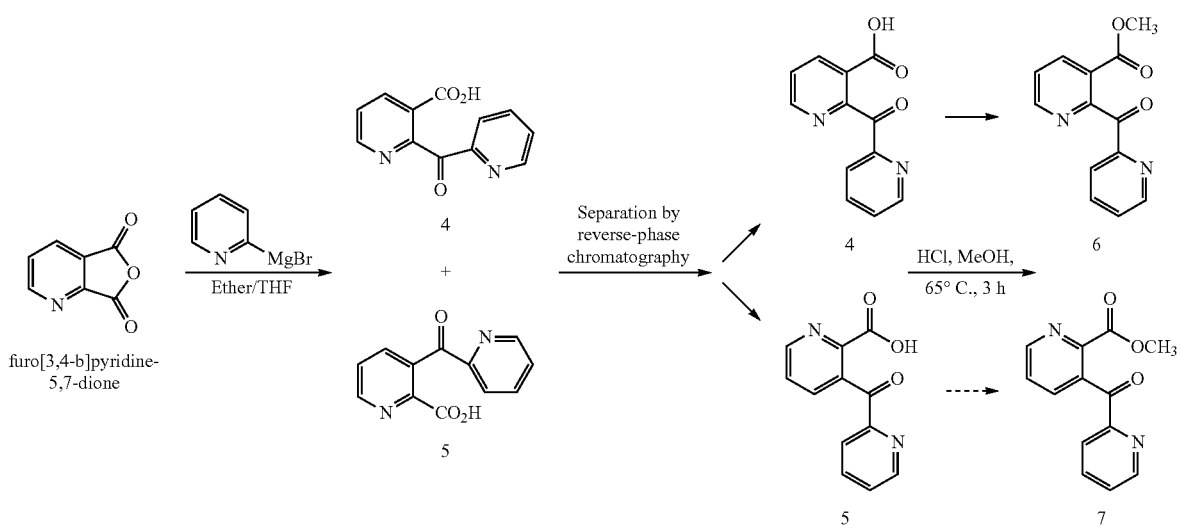

Synthetic Procedure

Furo[3,4-b]pyridine-5,7-dione

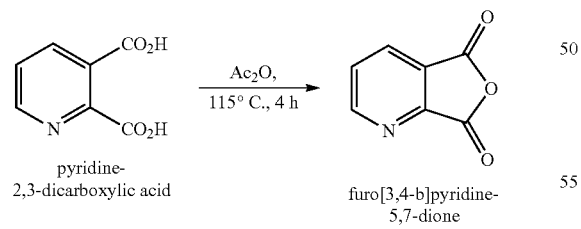

A mixture of pyridine-2,3-dicarboxylic acid (2 g, 12 mmol) and acetic anhydride was heated at 115° C. for 4 h. Excess reagent was removed under reduced pressure. The remaining solid was triturated with hot carbon tetrachloride. After cooling, the solid was collected by vacuum filtration and dried overnight under vacuum at 60° C. to give furo[3,4-b]pyridine-5,7-dione (1.55 g, 10.4 mmol). $^1$H NMR (400 MHz, DMSO-$d_6$) δ 9.10 (dd, J=4.9, 1.5 Hz, 1H), 8.50 (dd, J=7.8, 1.5 Hz, 1H), 7.90 (dd, J=7.8, 4.9 Hz, 1H).

2-Picolinoyl Nicotinic Acid and 3-Picolinoyl Picolinic Acid

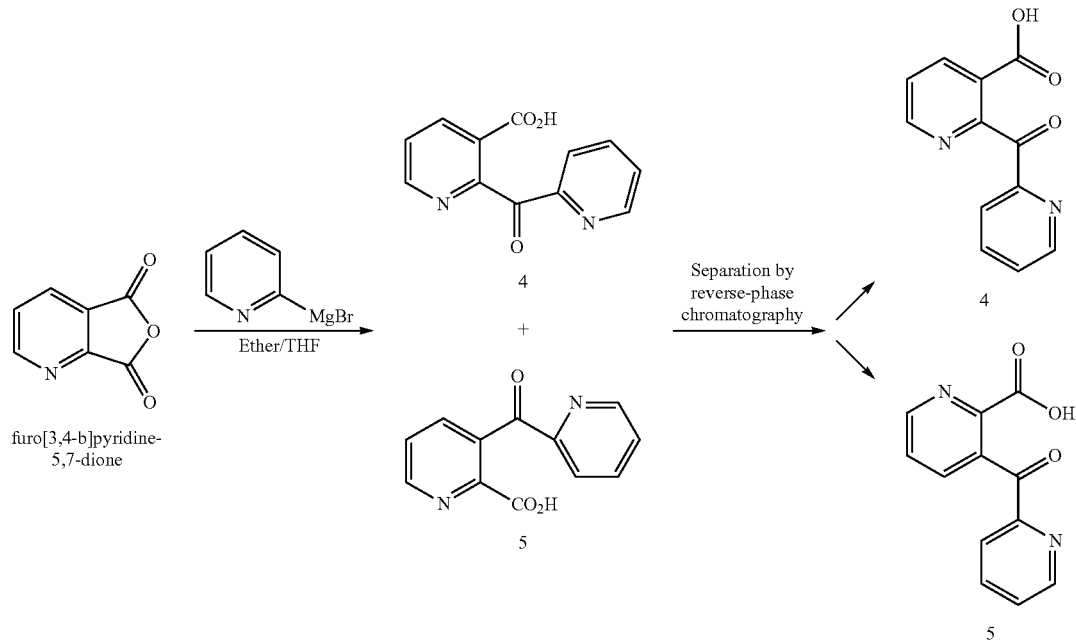

A solution of isopropyl magnesium bromide (2 M in tetrahydrofuran, 5 mL, 10 mmol) and ether (4 mL) was cooled to 0° C. A solution of 2-bromopyridine (3 mL, 30 mmol) in ether (4 mL) was added drop wise over 15 minutes. Subsequent to the completion of the addition, the cooling bath was removed from the reaction flask and the reaction mixture was stirred an additional 3.5 h at ambient temperature, resulting in a solution of 2-pyridyl magnesium bromide.

A solution of furo[3,4-b]pyridine-5,7-dione (4.5 g, 30 mmol) in ether (20 mL) and tetrahydrofuran (20 mL) was cooled to −78° C. The freshly prepared 2-pyridyl magnesium bromide was added drop wise over a 45-min period. The reaction mixture was stirred at −78° C. for 15 minutes, warmed to 0° C., stirred at 0° C. for 2 h and then quenched carefully with 40 mL of water. After stirring overnight, the reaction mixture was added to a separatory funnel. The layers were separated. LCMS revealed that the product was dispersed in both the aqueous and the organic layers. Each layer was separately concentrated under reduced pressure. The crude material from each layer was purified by reverse phase flash chromatography eluting with water-methanol, 10-80% over 19 minutes. Like fractions of each of the two picolinic acid products were combined and concentrated under reduced pressure. Identity of the 2-picolinoyl nicotinic acid product was confirmed by LCMS and retention time by comparing to an authentic sample. 2-Picolinoyl nicotinic acid (0.64 g, 0.027 mmol) was collected and used without further purification. A small amount (<50 mg) of 3-picolinoyl picolinic acid was also collected from separate fractions.

Methyl 2-picolinoyl Nicotinate

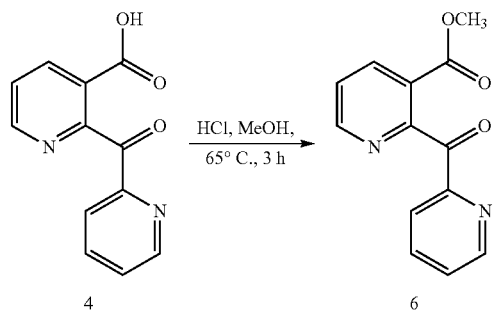 [SMILES: O=C(O)c1cccnc1C(=O)c1ccccn1 ; COC(=O)c1cccnc1C(=O)c1ccccn1]

A solution of 2-picolinoyl nicotinic acid (640 mg, 2.69 mmol) in 10 mL of 1.25 M methanolic HCl was heated in a sealed tube for at 60° C. for 3 h. After cooling to ambient temperature, excess solvent and reagent were removed under reduced pressure. The residue was partitioned between 20 ml of ethyl acetate and 20 mL 10% aqueous sodium carbonate. The aqueous layer was extracted further with 3×20 mL of ethyl acetate. The combined organic layers were dried over anhydrous sodium sulfate, filtered, concentrated under reduced pressure and purified by normal phase flash chromatography eluting with 0-2.5% methanol in dichloromethane. Like fractions were combined and concentrated under reduced pressure to give methyl 2-picolinoyl nicotinate (200 mg, 0.83 mmol). $^1$H NMR (400 MHz, Chloroform-d) δ 8.83 (dd, J=4.8, 1.6 Hz, 1H), 8.55 (ddd, J=4.8, 1.7, 0.9 Hz, 1H), 8.39-8.27 (m, 2H), 7.91 (td, J=7.7, 1.7 Hz, 1H), 7.49 (dd, J=8.0, 4.8 Hz, 1H), 7.43 (ddd, J=7.6, 4.8, 1.2 Hz, 1H), 3.67 (s, 3H). LCMS: (M+H)$^+$, 243.

In one variation the Rilyazines RL-10 and RL-11 may be prepared by reaction of the methyl 2-picolinoylnicotinate 6, with an appropriately-substituted hydrazine, and the ketone-Rilyazine may then be further converted to the thione-Rilyazine with Lawesson Reagent, Synthetic Scheme 3.

Scheme 3:

6-Benzyl-8-(pyridin-2-yl)pyrido[2,3-d]pyridazin-5(6H)-one, RL-10

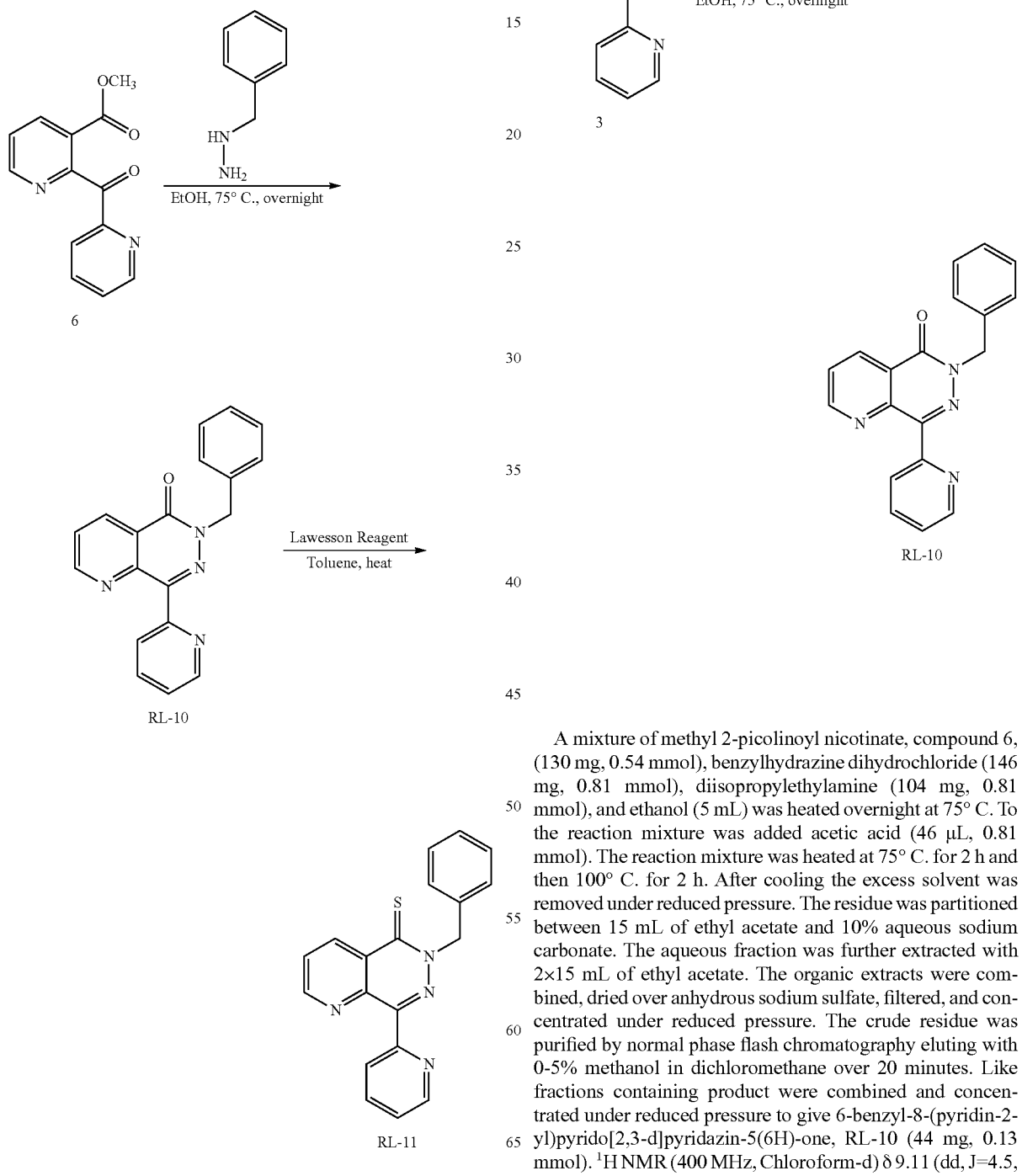

A mixture of methyl 2-picolinoyl nicotinate, compound 6, (130 mg, 0.54 mmol), benzylhydrazine dihydrochloride (146 mg, 0.81 mmol), diisopropylethylamine (104 mg, 0.81 mmol), and ethanol (5 mL) was heated overnight at 75° C. To the reaction mixture was added acetic acid (46 μL, 0.81 mmol). The reaction mixture was heated at 75° C. for 2 h and then 100° C. for 2 h. After cooling the excess solvent was removed under reduced pressure. The residue was partitioned between 15 mL of ethyl acetate and 10% aqueous sodium carbonate. The aqueous fraction was further extracted with 2×15 mL of ethyl acetate. The organic extracts were combined, dried over anhydrous sodium sulfate, filtered, and concentrated under reduced pressure. The crude residue was purified by normal phase flash chromatography eluting with 0-5% methanol in dichloromethane over 20 minutes. Like fractions containing product were combined and concentrated under reduced pressure to give 6-benzyl-8-(pyridin-2-yl)pyrido[2,3-d]pyridazin-5(6H)-one, RL-10 (44 mg, 0.13 mmol). $^1$H NMR (400 MHz, Chloroform-d) δ 9.11 (dd, J=4.5, 1.8 Hz, 2H), 8.89 (d, J=3.9 Hz, 2H), 8.77 (dd, J=8.1, 1.8 Hz, 1H), 7.91 (s, 2H), 7.68 (dd, J=8.1, 4.5 Hz, 1H), 7.49 (dd, J=25.2, 5.7 Hz, 3H), 7.37-7.24 (m, 5H), 5.53 (s, 2H). LCMS: (M+H)⁺, 316.

6-Benzyl-8-(pyridin-2-yl)pyrido[2,3-d]pyridazine-5(6H)-thione, RL-11

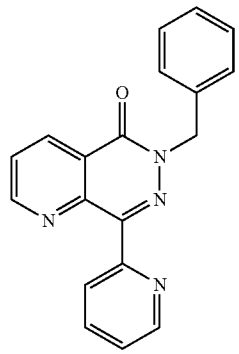

RL-10

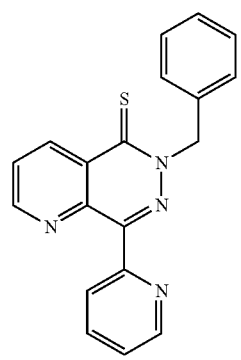

RL-11

A mixture of 6-benzyl-8-(pyridin-2-yl)pyrido[2,3-d]pyridazin-5(6H)-one RL-10 (45 mg, 0.143 mmol), 2,4-bis(4-methoxyphenyl)-1,3,2,4-dithiadiphosphetane-2,4-disulfide (57 mg, 0.143 mmol), and 4 mL of toluene were heated to 115° C. for 2 h. Another 35 mg aliquot of 2,4-bis(4-methoxyphenyl)-1,3,2,4-dithiadiphosphetane-2,4-disulfide was added and the heating was continued for 2 h. Still another 35 mg aliquot of 2,4-bis(4-methoxyphenyl)-1,3,2,4-dithiadiphosphetane-2,4-disulfide was added and heating continued for an additional 2 h. After cooling, the reaction mixture was poured into 15 mL of saturated brine and then extracted with 4×20 mL of ethyl acetate. The combined organic extracts were dried over anhydrous sodium sulfate, filtered, concentrated under reduced pressure, and dried overnight at 60° C. under vacuum to give 6-benzyl-8-(pyridine-2-yl)pyrido[2,3-d]pyridazine-5(6H)-thione RL-11 (31 mg, 0.94 mmol). ¹H NMR (400 MHz, Chloroform-d) δ 9.25 (dd, J=8.4, 1.7 Hz, 1H), 9.19-9.12 (m, 1H), 9.03 (s, 1H), 8.13 (bd, J=57.3 Hz, 1H), 7.72 (dd, J=8.4, 4.4 Hz, 1H), 7.64-7.52 (m, 3H), 7.40-7.25 (m, 4H), 6.17 (s, 2H). LCMS: (M+H)⁺, 331.

In yet another variation, the ketone-Rilyazines 10 or 11 may be prepared according to Scheme 4. Further conversion may be effected by reaction with Lawesson Reagent to yield the thione-Rilyazines 12 or 13.

Scheme 4:

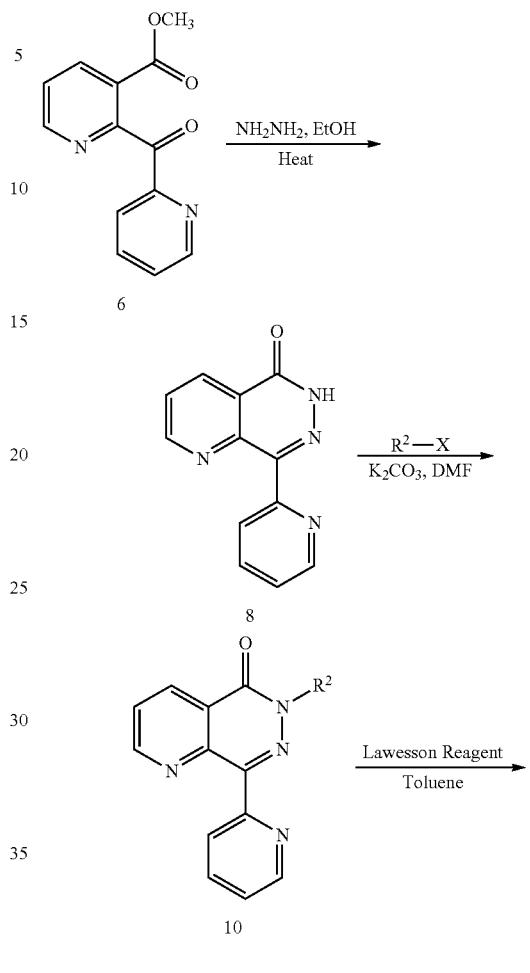

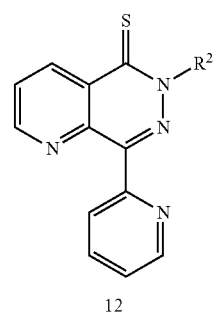

12

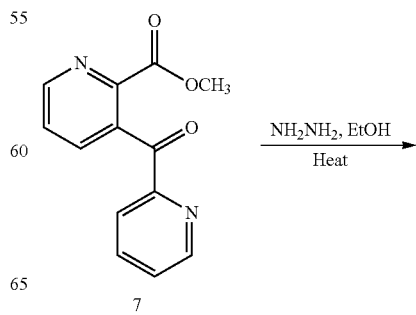

7

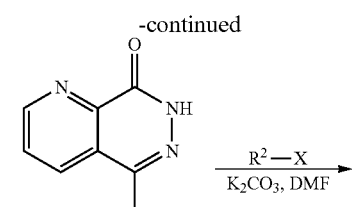

9

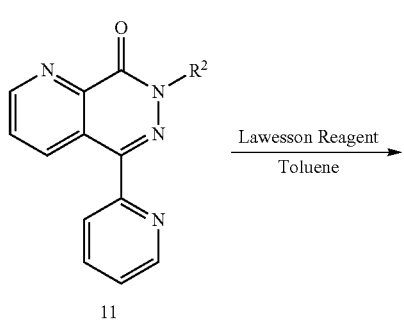

11

8-(Pyridin-2-yl)pyrido[2,3-d]pyridazin-5(6H)-one

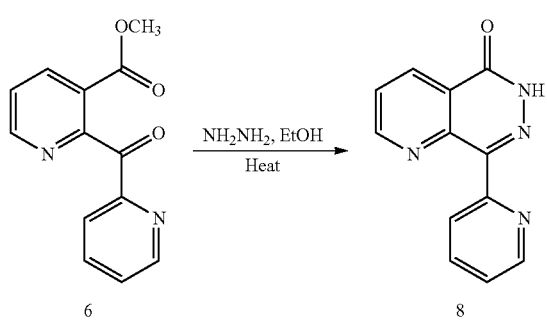 [SMILES: COC(=O)c1cccnc1C(=O)c1ccccn1 ; O=c1[nH]nc(-c2ccccn2)c2ncccc12]

6     8

A mixture of methyl 2-picolinoyl nicotinate (206 mg, 0.85 mmol), hydrazine hydrate (50 µL, 1.02 mmol), and ethanol (10 mL) was heated at 75° C. in a sealed tube for 1 h. After cooling, the solid was filtered and dried at 60° C. for 1 h to give 8-(pyridin-2-yl)pyrido[2,3-d]pyridazin-5(6H)-one (120 mg, 0.54 mmol), compound 8. $^1$H NMR (400 MHz, DMSO-$d_6$) δ 13.13 (s, 1H), 9.07 (dd, J=4.5, 1.8 Hz, 1H), 8.70-8.60 (m, 2H), 7.91 (td, J=7.7, 1.8 Hz, 1H), 7.84 (dd, J=8.1, 4.5 Hz, 1H), 7.72 (dt, J=7.8, 1.1 Hz, 1H), 7.47 (ddd, J=7.6, 4.8, 1.2 Hz, 1H). LCMS; (M+H)$^+$, 225.

6-Ethyl-8-(pyridin-2-yl)pyrido[2,3-d]pyridazin-5(6H)-one, RL-6

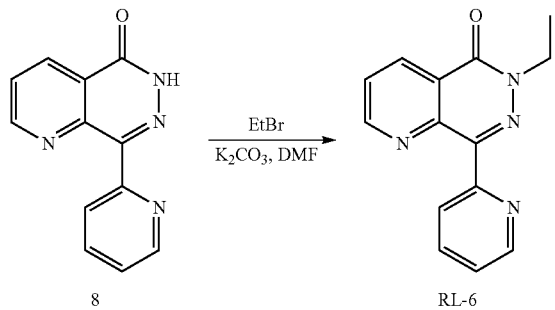 [SMILES: "EtBr" ; O=c1[nH]nc(-c2ccccn2)c2ncccc12 ; CCn1nc(-c2ccccn2)c2ncccc2c1=O]

8     RL-6

A mixture of 8-(pyridin-2-yl)pyrido[2,3-d]pyridazin-5(6H)-one 8 (50 mg, 0.22 mmol), ethyl bromide (20 µL, 0.27 mmol), potassium carbonate (303 mg, 2.2 mmol), and dimethylformamide (1.5 mL) was heated in a sealed tube at 60° C. for 30 minutes. After cooling to ambient temperature, the reaction mixture was poured into 15 mL of saturated brine and extracted with 3×20 mL of ethyl acetate. The combined organic extracts were dried over anhydrous sodium sulfate, filtered and concentrated under reduced pressure. The residue was purified by normal phase flash chromatography eluting with 0-10% methanol in dichloromethane over 16 minutes Like fractions containing product were pooled, concentrated under reduced pressure, and dried at 60° C. overnight to give 6-ethyl-8-(pyridin-2-yl)pyrido[2,3-d]pyridazin-5(6H)-one (46 mg, 0.19 mmol), RL-6. $^1$H NMR (400 MHz, Chloroform-d) δ 9.15 (s, 1H), 9.02 (s, 1H), 8.80 (d, J=8.3 Hz, 1H), 8.23 (s, 1H), 8.04 (s, 1H), 7.71 (dd, J=8.1, 4.6 Hz, 1H), 7.56 (s, 1H), 4.48 (q, J=7.1 Hz, 2H), 1.52 (t, J=7.2 Hz, 3H). LCMS: (M+H)$^+$, 253.

6-Benzyl-8-(pyridin-2-yl)pyrido[2,3-d]pyridazin-5(6H)-one, RL-10

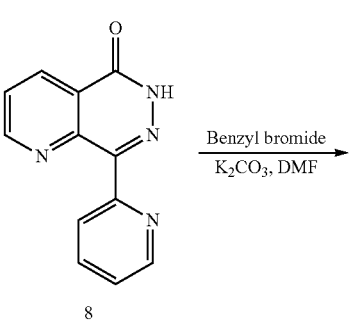

8

7.83 (m, 2H), 7.74-7.59 (m, 2H), 7.47-7.37 (m, 1H), 7.33-7.27 (m, 1H), 7.21-7.13 (m, 1H), 5.68 (s, 2H). LCMS: (M+H)+, 316.

6-Ethyl-8-(pyridin-2-yl)pyrido[2,3-d]pyridazine-5(6H)-thione, RL-7

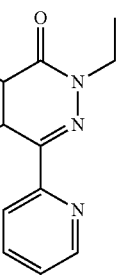

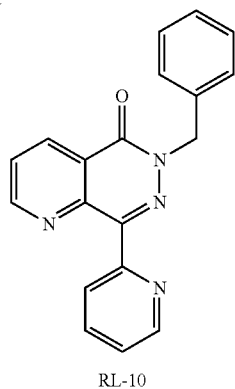

RL-10 was prepared by reaction of 8 with benzyl bromide, similarly to the method described for synthesis of RL-6. ¹H NMR (400 MHz, Chloroform-d) δ 9.09 (dd, J=4.5, 1.8 Hz, 1H), 8.84 (d, J=4.5 Hz, 1H), 8.77 (dd, J=8.1, 1.8 Hz, 1H), 7.90-7.79 (m, 2H), 7.67 (dd, J=8.1, 4.5 Hz, 1H), 7.55-7.47 (m, 2H), 7.42 (ddd, J=7.2, 4.9, 1.5 Hz, 1H), 7.36-7.23 (m, 3H), 5.51 (s, 2H). LCMS: (M+H)+, 315.

8-(Pyridin-2-yl)-6-(pyridin-2-ylmethyl)pyrido[2,3-d]pyridazin-5(6H)-one, RL-14

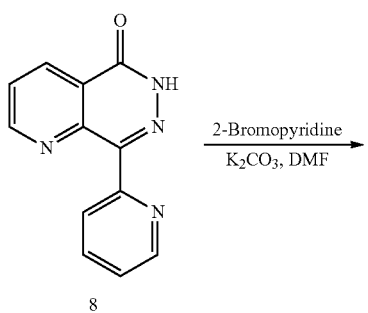

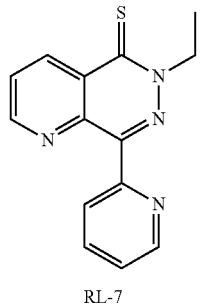

RL-6 was converted to the corresponding thione RL-7, similarly to the method described for thiation of RL-10 to yield RL-11 and as shown in Scheme 3. ¹H NMR (400 MHz, DMSO-d₆) δ 9.08 (s, 1H), 8.96-8.90 (m, 1H), 8.72 (s, 1H), 7.96-7.83 (m, 2H), 7.57-7.50 (m, 1H), 4.26 (q, J=6.2, 5.8 Hz, 2H), 1.36 (d, J=6.6 Hz, 3H). LCMS: (M+H)+, 269.

8-(Pyridin-2-yl)-6-(pyridin-2-ylmethyl)pyrido[2,3-d]pyridazine-5(6H)-thione, RL-15

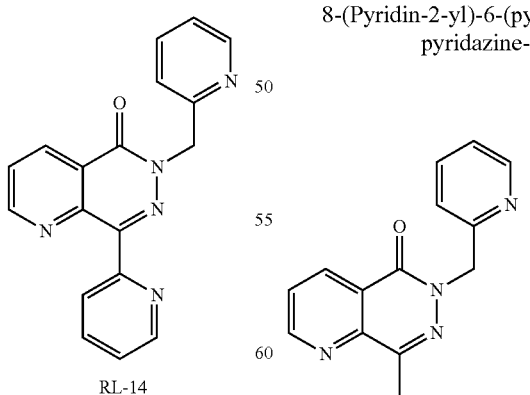

RL-14 was prepared by reaction of 8 with 2-bromopyridine, similarly to the method described for synthesis of RL-6. ¹H NMR (400 MHz, Chloroform-d) δ 9.18-9.07 (m, 1H), 8.88-8.74 (m, 2H), 8.54 (ddd, J=4.9, 1.7, 0.9 Hz, 1H), 7.92-

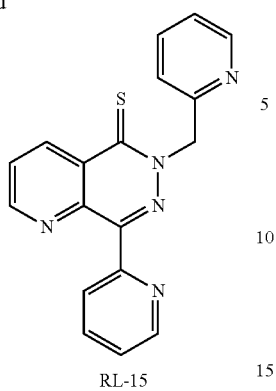

RL-15

RL-14 was converted to the corresponding thione RL-15, similarly to the method described for thiation of RL-9 to yield RL-10 as shown in Scheme 3. $^1$H NMR (400 MHz, Chloroform-d) δ 9.23 (d, J=8.3 Hz, 1H), 9.15 (d, J=4.3 Hz, 1H), 8.95 (s, 1H), 8.58 (d, J=4.6 Hz, 1H), 8.17 (s, 1H), 8.00 (t, J=7.3 Hz, 1H), 7.82-7.65 (m, 2H), 7.59-7.49 (m, 1H), 7.41 (d, J=8.1 Hz, 1H), 7.28 (d, J=7.7 Hz, 1H), 6.33 (s, 2H). LCMS: (M+H)$^+$, 332.

In yet another variation, the ketone-Rilyazines RL-8, RL-12 and RL-16 may be prepared via the intermediate 9, synthesized according to Scheme 5. The reactions used to synthesize N,N-diethylpicolinamide 14 and N,N-diethyl-3-picolinoylpicolinamide 15 are adapted from Tetrahedron (1995) Vol. 51, No. 4, pp. 1259-1264.

Scheme 5:

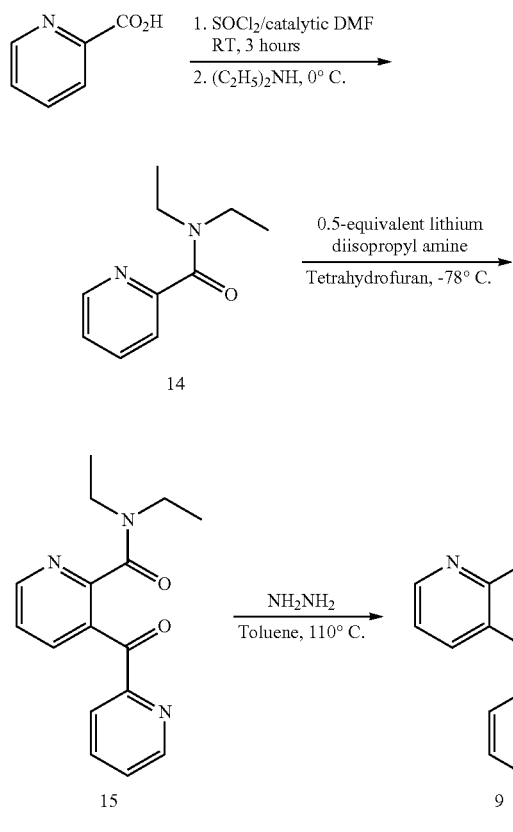

N,N-Diethylpicolinamide, Compound 14

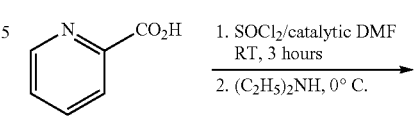

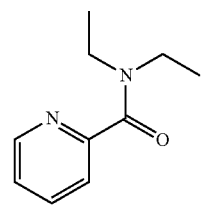

14

A slurry of picolinic acid (10.2 g, 83.3 mmol) in 100 mL of thionyl chloride was stirred at ambient temperature for 10 min. Dimethylformamide (0.5 mL) was carefully added dropwise via a syringe. After 3 hours the mixture became a clear, homogeneous solution. Excess thionyl chloride and dimethylformamide were removed under reduced pressure. The residue was azeotroped 3× with dry toluene, dissolved in 100 mL of dichloromethane, cooled to 0° C. and treated dropwise with diethylamine (34.5 mL, 330 mmol) over a 12 minute period. The reaction mixture was stirred for 72 hours at ambient temperature and then filtered through a pad of Celite® filter aid. The filtrate was poured into 200 mL of water. The organic phase was collected and the aqueous phase was extracted with 3×100 mL of dichloromethane. The combined organic extracts were washed successively with 1N NaOH, water, and brine, dried over sodium sulfate, filtered and concentrated under reduced pressure. The crude material was purified by normal phase flash chromatography eluting with 100% ethyl acetate. Like fractions containing product were combined and concentrated under reduced pressure to give N,N diethylpicolinamide 14. (12.6 g, 70.8 mmol). $^1$H NMR (400 MHz, Chloroform-d) δ 8.47 (ddd, J=4.8, 1.7, 1.0 Hz, 1H), 7.71-7.62 (m, 1H), 7.45 (ddd, J=7.8, 1.9, 0.8 Hz, 1H), 7.27-7.17 (m, 1H), 3.46 (q, J=7.1 Hz, 2H), 3.26 (q, J=7.1 Hz, 2H), 1.16 (t, J=7.1 Hz, 3H), 1.04 (t, J=7.1 Hz, 3H). LCMS: (M+H)$^+$, 179.

N,N-Diethyl-3-picolinoylpicolinamide, Compound 15

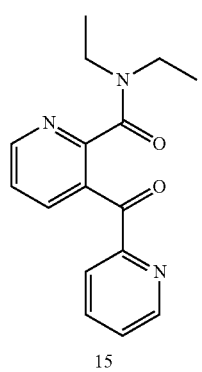

A solution of n-butyllithium (1.6M in hexane, 3.65 mL, 5.85 mmol) was added dropwise over a 5-minute period to a solution of diisopropylamine (818 µL, 5.85 mmol) in 20 mL of anhydrous tetrahydrofuran held at −78° C. and under nitrogen. The reaction was warmed to 0° C., held at that temperature for 15 min, and then cooled to −78° C. The resulting solution was added dropwise over a 10 minute period to a solution of N,N-diethylpicolinamide 14 (2.09 g, 11.7 mmol) in 20 mL of anhydrous tetrahydrofuran under nitrogen at −78° C. The reaction was then allowed to warm slowly overnight to ambient temperature and then quenched with 10 mL of water and 10 mL of saturated brine. The reaction mixture was extracted with 3×30 mL of ethyl acetate. The combined organic extracts were dried over sodium sulfate, filtered and concentrated under reduced pressure. The resulting oil was crystallized from ethanol/hexanes to give N,N-diethyl-3-picolinoylpicolinamide 12 (750 mg, 2.64 mmol). $^1$H NMR (400 MHz, DMSO-$d_6$) δ 8.69-8.60 (m, 1H), 8.62-8.53 (m, 1H), 8.09-7.95 (m, 3H), 7.66-7.53 (m, 2H), 3.43-3.24 (m, 2H), 3.07 (q, J=7.1 Hz, 2H), 1.22 (t, J=7.0 Hz, 2H), 0.55 (t, J=7.1 Hz, 2H). LCMS: (M+H)$^+$, 284.

5-(Pyridin-2-yl)pyrido[2,3-d]pyridazin-8(7H)-one, Compound 9

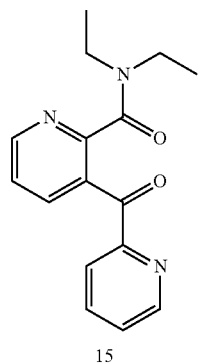

A mixture of N,N-diethyl-3-picolinoylpicolinamide 15 (550 mg, 1.94 mmol), hydrazine hydrate (282 µL, 5.82 mmol), and diethylene glycol (4 mL) was heated to 150° C. for 1 h and then 175° C. for 30 min. The hot solution was poured into 12 mL of water and the pH was adjusted to ~8 with 1N HCl. The mixture was placed in the freezer overnight. The resulting precipitate was collected by vacuum filtration and the solid was dried overnight at 60° C. under vacuum, to give 5-(pyridin-2-yl)pyrido[2,3-d]pyridazin-8(7H)-one 9 (298 mg, 1.33 mmol). $^1$H NMR (400 MHz, DMSO-$d_6$) δ 9.07 (dd, J=4.4, 1.7 Hz, 1H), 8.91 (dd, J=8.4, 1.7 Hz, 1H), 8.72 (ddd, J=4.8, 1.8, 0.9 Hz, 1H), 8.04-7.95 (m, 1H), 7.92-7.84 (m, 2H), 7.52 (ddd, J=7.5, 4.8, 1.2 Hz, 1H). LCMS: (M+H)$^+$, 225.

7-Ethyl-5-(pyridin-2-yl)pyrido[2,3-d]pyridazin-8 (7H)-one, RL-8

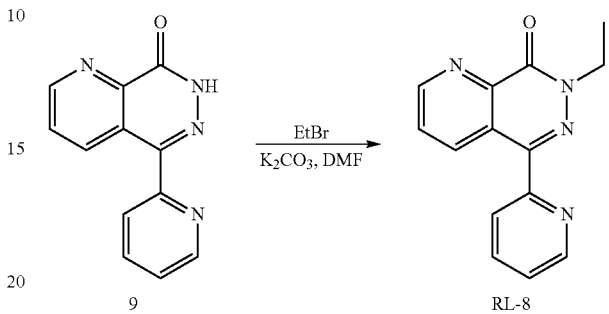

5-(Pyridin-2-yl)pyrido[2,3-d]pyridazin-8(7H)-one 9 was reacted with ethyl bromide under basic conditions to yield the corresponding ketone-Rilyazine RL-8, in a reaction similarly to that described for conversion of compound 8 to RL-6, and as shown in Synthetic Scheme 4. $^1$H NMR (400 MHz, DMSO-$d_6$) δ 9.08 (dd, J=4.4, 1.6 Hz, 1H), 8.94 (dd, J=8.4, 1.6 Hz, 1H), 8.73 (ddd, J=4.8, 1.7, 0.9 Hz, 1H), 8.01 (td, J=7.7, 1.8 Hz, 1H), 7.97-7.83 (m, 2H), 7.53 (ddd, J=7.5, 4.8, 1.3 Hz, 1H), 4.26 (q, J=7.2 Hz, 2H), 1.35 (t, J=7.2 Hz, 3H). LCMS: (M+H)$^+$, 269.

7-Benzyl-5-(pyridin-2-yl)pyrido[2,3-d]pyridazin-8 (7H)-one, RL-12

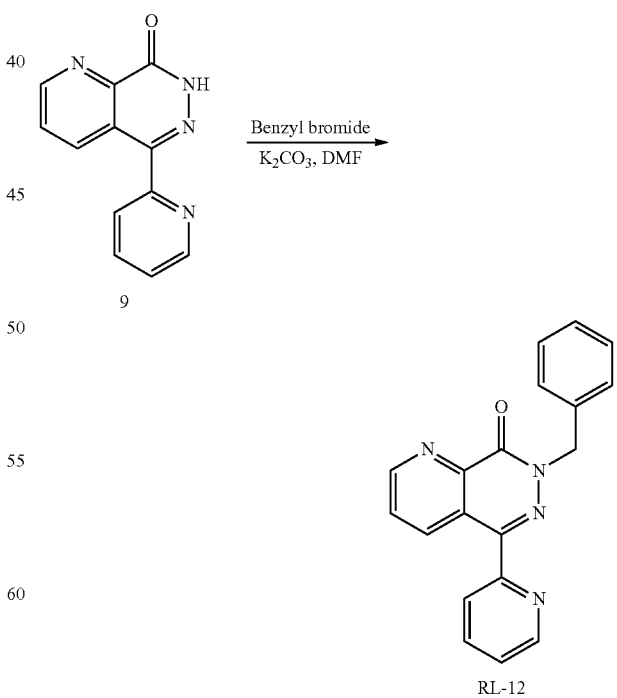

Compound 9 was reacted with benzyl bromide under basic conditions to yield the corresponding ketone-Rilyazine RL-12, in a reaction similarly to that described for conversion of compound 8 to RL-6, and as shown in Scheme 4. ¹H NMR (400 MHz, Chloroform-d) δ 9.18-9.07 (m, 2H), 8.71 (ddd, J=4.9, 1.7, 1.0 Hz, 1H), 7.95-7.82 (m, 2H), 7.69 (dd, J=8.4, 4.4 Hz, 1H), 7.58-7.51 (m, 3H), 7.40 (ddd, J=7.3, 4.9, 1.5 Hz, 1H), 7.37-7.23 (m, 4H), 5.55 (s, 2H). LCMS: (M+H)⁺, 331.

5-(Pyridin-2-yl)-7-(pyridin-2-ylmethyl)pyrido[2,3-d]pyridazin-8(7H)-one, RL-16

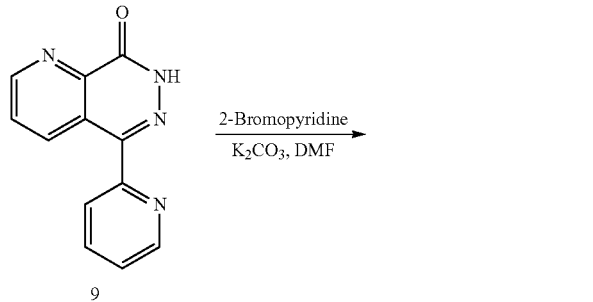

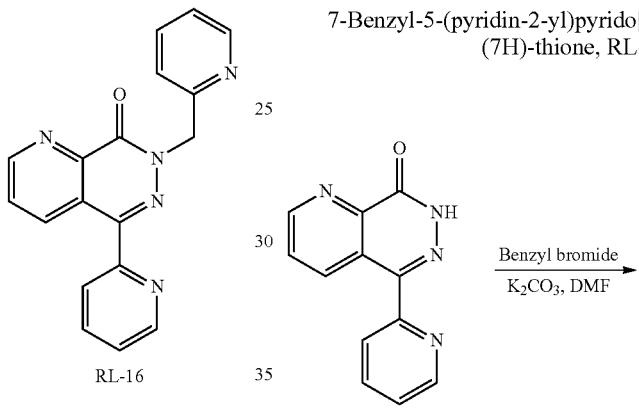

Compound 9 was reacted with 2-bromopyridine under basic conditions to yield the corresponding ketone-Rilyazine RL-16, in a reaction similarly to that described for conversion of compound 8 to RL-6, and as shown in Scheme 4. ¹H NMR (400 MHz, Chloroform-d) δ 9.21-9.09 (m, 2H), 8.71 (ddd, J=4.9, 1.8, 0.9 Hz, 1H), 8.59-8.52 (m, 1H), 7.97-7.89 (m, 1H), 7.84 (td, J=7.7, 1.7 Hz, 1H), 7.73 (dd, J=8.3, 4.4 Hz, 1H), 7.64 (td, J=7.7, 1.8 Hz, 1H), 7.43-7.34 (m, 2H), 7.28-7.15 (m, 2H), 5.73 (s, 2H). LCMS: (M+H)⁺, 332.

The following example is illustrative of a typical thiation procedure for this series of compounds.

7-Ethyl-5-(pyridin-2-yl)pyrido[2,3-d]pyridazine-8(7H)-thione, RL-9

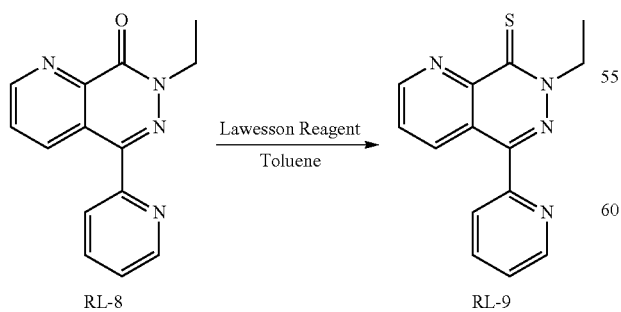

A mixture of 7-ethyl-5-(pyridin-2-yl)pyrido[2,3-d]pyridazin-8(7H)-one RL-8 (90 mg, 0.36 mmol), 2,4-bis(4-methoxyphenyl)-1,3,2,4-dithiadiphosphetane-2,4-disulfide (145 mg, 0.36 mmol), and toluene (8 mL) was heated to 115° C. for 3.5 h. After cooling to ambient temperature, the reaction mixture was diluted with 20 mL of ethyl acetate and washed with a 1:1 solution of saturated brine/1 N NaOH. The organic phase was dried over anhydrous magnesium sulfate, filtered, concentrated under reduced pressure and purified by normal phase flash chromatography eluting with 0-10% methanol in dichloromethane over 22 minutes. Like fractions containing the desired product were pooled, concentrated under reduced pressure, and dried overnight at 60° C. under vacuum to give 7-ethyl-5-(pyridin-2-yl)pyrido[2,3-d]pyridazine-8(7H)-thione RL-9 (52 mg, 0.20 mmol). ¹H NMR (400 MHz, DMSO-d₆) δ 9.17 (dd, J=4.3, 1.7 Hz, 1H), 8.98 (dd, J=8.3, 1.7 Hz, 1H), 8.77 (ddd, J=4.8, 1.7, 1.0 Hz, 1H), 8.08-7.97 (m, 2H), 7.91 (dd, J=8.3, 4.3 Hz, 1H), 7.59 (ddd, J=7.3, 4.8, 1.5 Hz, 1H), 4.86 (q, J=7.1 Hz, 2H), 1.45 (t, J=7.1 Hz, 3H).

The following compounds were made in an analogous fashion:

7-Benzyl-5-(pyridin-2-yl)pyrido[2,3-d]pyridazine-8(7H)-thione, RL-13

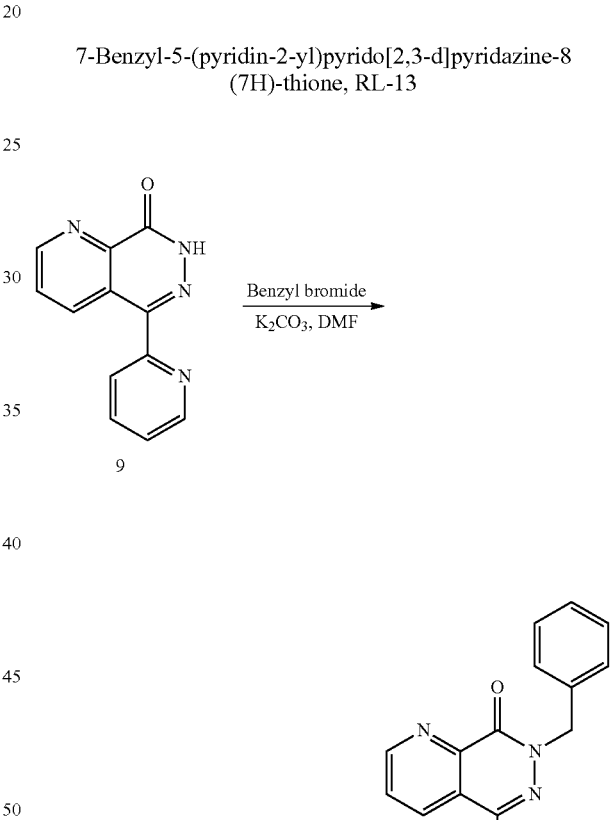

¹H NMR (400 MHz, Chloroform-d) δ 9.26-9.15 (m, 2H), 8.78 (ddd, J=4.9, 1.6, 1.0 Hz, 1H), 8.00-7.93 (m, 2H), 7.74 (dd, J=8.3, 4.4 Hz, 1H), 7.61-7.46 (m, 3H), 7.37-7.22 (m, 3H), 6.18 (s, 2H).

5-(Pyridin-2-yl)-7-(pyridin-2-ylmethyl)pyrido[2,3-d]pyridazine-8(7H)-thione, RL-17

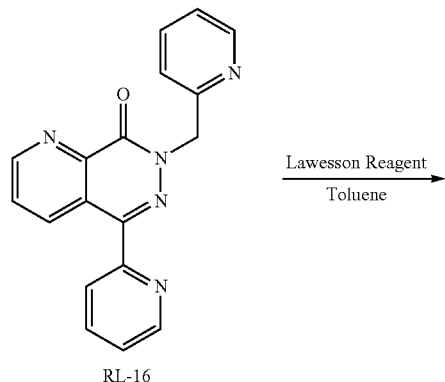

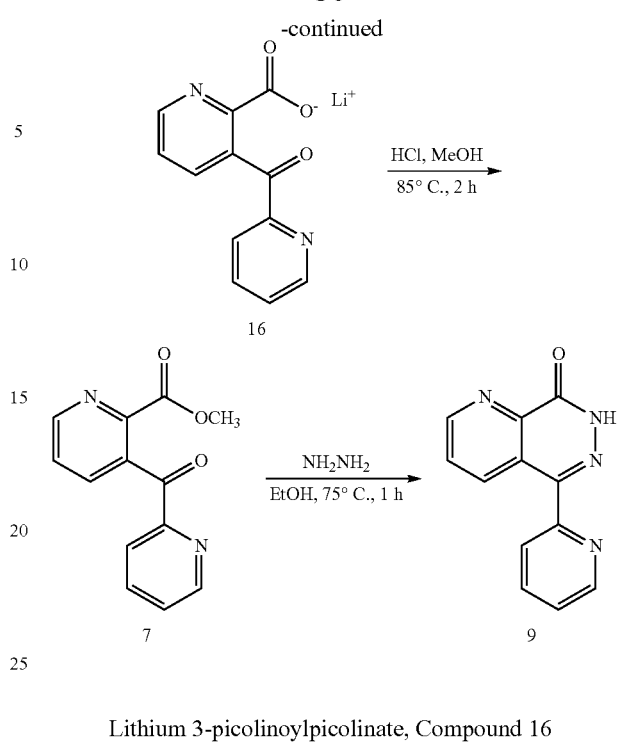

Lithium 3-picolinoylpicolinate, Compound 16

¹H NMR (400 MHz, DMSO-d6) δ 9.18 (dd, J=4.3, 1.7 Hz, 1H), 9.03 (dd, J=8.3, 1.7 Hz, 1H), 8.77 (ddd, J=4.8, 1.8, 0.9 Hz, 1H), 8.44 (ddd, J=4.8, 1.8, 0.9 Hz, 1H), 8.06-7.86 (m, 3H), 7.72 (td, J=7.7, 1.8 Hz, 1H), 7.58 (ddd, J=7.6, 4.8, 1.2 Hz, 1H), 7.33-7.21 (m, 2H), 6.15 (s, 2H).

Scheme 6 is an alternative method for the regiospecific synthesis of the methyl 3-picolinoylpicolinate 7 and 5-(pyridin-2-yl)pyrido[2,3-d]pyridazin-8(7H)-one 6.

Scheme 6:

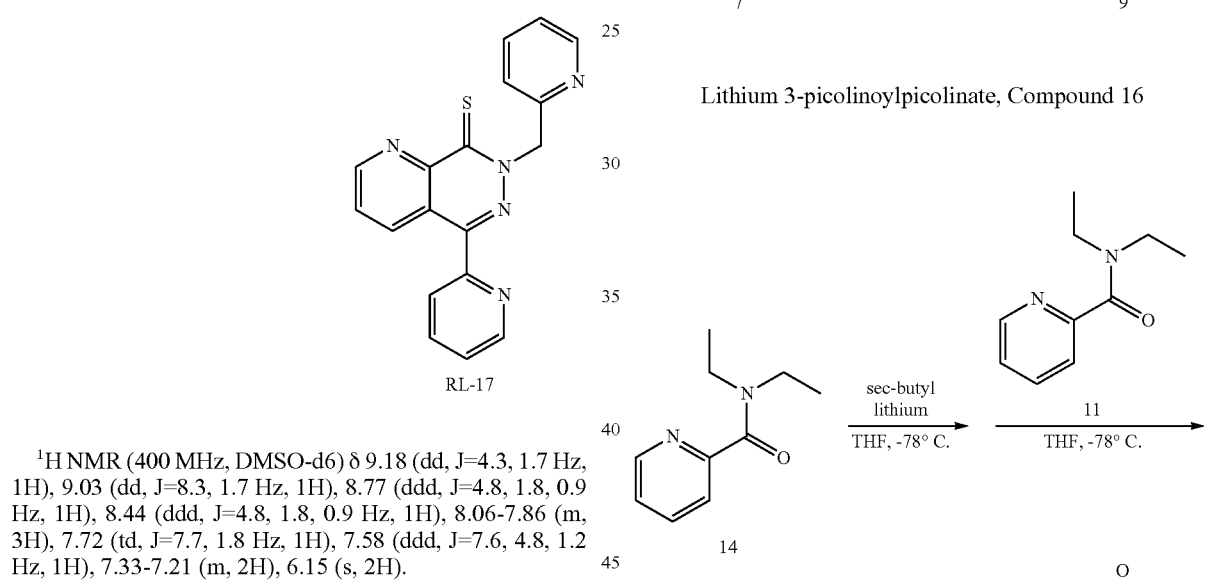

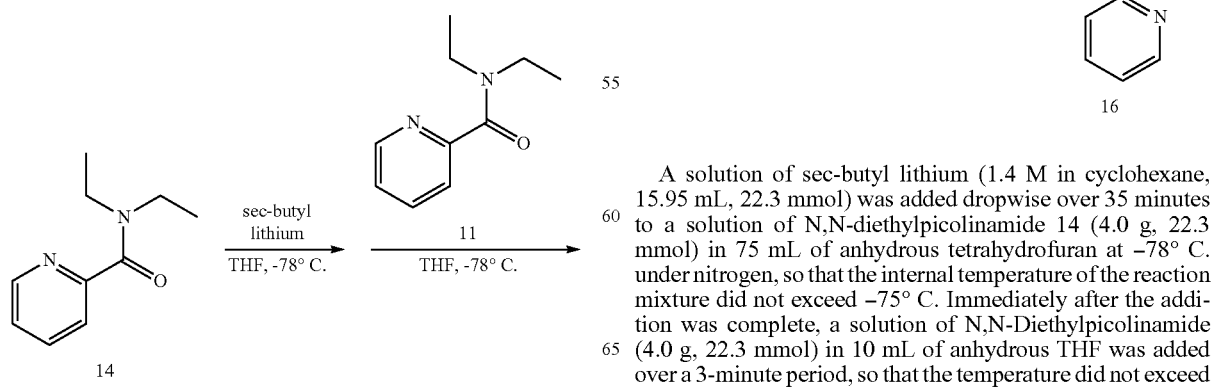

A solution of sec-butyl lithium (1.4 M in cyclohexane, 15.95 mL, 22.3 mmol) was added dropwise over 35 minutes to a solution of N,N-diethylpicolinamide 14 (4.0 g, 22.3 mmol) in 75 mL of anhydrous tetrahydrofuran at −78° C. under nitrogen, so that the internal temperature of the reaction mixture did not exceed −75° C. Immediately after the addition was complete, a solution of N,N-Diethylpicolinamide (4.0 g, 22.3 mmol) in 10 mL of anhydrous THF was added over a 3-minute period, so that the temperature did not exceed −70° C. The reaction mixture was stirred at −78° C. for 2.3 h and allowed to warm to ambient temperature over 45 minutes. After stirring at ambient temperature for 15 minutes, 50 mL of water was added all at once. The reaction was stirred overnight at ambient temperature. The reaction mixture was added to a separatory funnel and the layers were separated. The aqueous layer was washed further with 3×50 mL of ethyl acetate. LCMS of each of the layers revealed that product resided in the aqueous layer. The aqueous layer was concentrated under reduced pressure to give 2.5 g of crude (~85% pure by LCMS) lithium 3-picolinoylpicolinate 16. This was used without further purification.

Methyl 3-picolinoylpicolinate, Compound 7

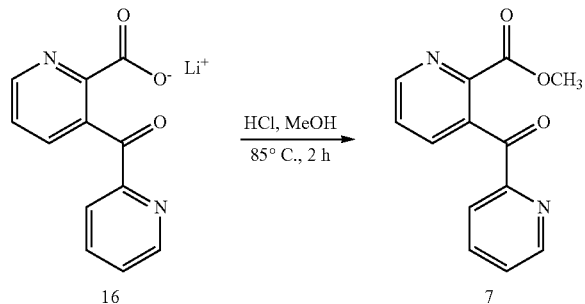 [SMILES: O=C(c1ccccn1)c1cccnc1C(=O)[O-] ; [Li+] ; COC(=O)c1ncccc1C(=O)c1ccccn1]

A mixture of 2.5 g of crude lithium 3-picolinoylpicolinate 16 was dissolved in 40 mL of 1.25 N HCl in methanol and heated in a sealed tube at 85° C. for 2 h. After cooling, the excess solvent and reagent were removed under reduced pressure and the crude material was partitioned between 20 mL of ethyl acetate and 20 mL of saturated aqueous sodium carbonate. The aqueous layer was further extracted with 2×20 mL of ethyl acetate. The combined organic layers were dried over anhydrous sodium sulfate, filtered and concentrated under reduced pressure. The crude residue was purified by normal-phase flash chromatography eluting with 50-100% ethyl acetate in hexane over 29 minutes. Like fractions containing product were pooled and concentrated under reduced pressure to give methyl 3-picolinoylpicolinate 7 (240 mg, 0.99 mmol), LCMS: $(M+H)^+$, 243.

8-(Pyridin-2-yl)pyrido[2,3-d]pyridazin-5(6H)-one, Compound 9

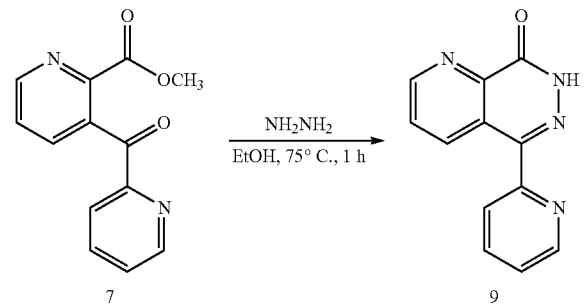 [SMILES: COC(=O)c1ncccc1C(=O)c1ccccn1 ; "NH2NH2" ; O=c1[nH]nc(-c2ccccn2)c2cccnc12]

A mixture of methyl 3-picolinoylpicolinate 7, (240 mg, 0.99 mmol), hydrazine hydrate (63 µL, 1.3 mmol) and 12 mL of absolute ethanol was heated to 75° C. in a sealed tube for 1 h. After cooling, the solid was collected by vacuum filtration and dried under air suction. The mother liquor was concentrated to dryness under reduced pressure and purified by normal phase flash chromatography eluting with 0-10% methanol in dichloromethane over approximately 20 minutes. Like fractions were combined and concentrated under reduced pressure and combined with the solid collected by filtration to give 8-(pyridin-2-yl)pyrido[2,3-d]pyridazin-5 (6H)-one 9 (150 mg, 0.67 mmol). $^1$H NMR (400 MHz, Methanol-$d_4$) δ 9.07 (dd, J=4.5, 1.6 Hz, 1H), 8.98 (dd, J=8.4, 1.6 Hz, 1H), 8.72 (ddd, J=4.9, 1.7, 1.0 Hz, 1H), 8.00 (ddd, J=7.9, 7.3, 1.7 Hz, 1H), 7.99-7.92 (m, 1H), 7.97-7.84 (m, 1H), 7.53 (ddd, J=7.3, 4.9, 1.5 Hz, 1H). LCMS: $(M+H)^+$, 225.

Biological Assays:

In vitro characterizing of the effects of rilyazine analogs on cell proliferation and apoptosis.

Screening of RL-1, RL-2, RL-3, and RL-4 was performed on a 60 cell line panel.

The screening is a two-stage process, beginning with the evaluation of all compounds against 60 cell lines at a single dose of $10^{-5}$ M.

RL-4 was evaluated against the 60 cell panel at five concentration levels, $10^{-8}$ M, $10^{-7}$ M, $10^{-6}$ M, $10^{-5}$ M and $10^{-4}$ M.

The human tumor cell lines of the cancer screening panel are grown in RPMI 1640 medium containing 5% fetal bovine serum and 2 mM L-glutamine. Cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 h prior to addition of experimental drugs.

After 24 h, two plates of each cell line are fixed in situ with TCA, to represent a measurement of the cell population for each cell line at the time of drug addition Time Zero (Tz). Experimental drugs are solubilized in dimethyl sulfoxide: glycerol 9:1 at 400-fold the desired final maximum test concentration and stored frozen at −70° C. prior to use. At the time of drug addition, an aliquot of frozen concentrate is thawed and diluted to twice the desired final maximum test concentration with complete medium containing 50 µg/ml gentamicin. Additional four, 10-fold or ½ log serial dilutions are made to provide a total of five drug concentrations plus control. Aliquots of 100 µl of these different drug dilutions are added to the appropriate microtiter wells already containing 100 µl of medium, resulting in the required final drug concentrations.

Positive control is prepared by adding the known antitumor agent adriamycin, NSC 123127, prepared and stored the same as the compounds for testing.

Following drug addition, the plates are incubated for an additional 48 h at 37° C., 5% $CO_2$, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA).

For the 1-dose 60 cell testing, the Growth Percent is calculated for each cell line/drug combination from the absorbance measurement for the no-drug control (C), the absorbance at time zero (Tz) and the absorbance measurement after incubation of the cells in the presence of drug (Ti):

Growth Percent=[(Ti−Tz)/(C−Tz)]×100 for cell line/drug combinations for which Ti≥Tz.

Growth Percent=[(Ti−Tz)/Tz]×100 for cell line/drug combinations for which Ti<Tz.

Calculation of the Growth Percent by these equations allows detection of both growth inhibition (Growth Percent values between 0 and 100) and lethality (Growth Percent values less than 0). For example, a Growth Percent value of 100 means no growth inhibition. A Growth Percent value of 40 would mean 60% growth inhibition. A Growth Percent value of 0 means no net growth over the course of the experiment, or "cytostatic", no change by growth or cell death. A Growth Percent value of −40 would mean 40% lethality. A Growth Percent value of −100 means all cells are dead.

For 1-dose 60 cell testing, the Mean Growth Percent, Delta and Range across all 60 cell lines are also calculated. The Deviation of each cell line/drug combination from the Mean is also calculated and plotted:

Deviation=Mean Growth Percent−Growth Percent

For a cell line/drug combination in which the deviation is near zero, there is little specificity of that cell line/drug combination. If the deviation is large for any particular cell line/drug combination, the drug may have effects that are specific to that particular cell line. A large Delta and/or large Range are also indicative of specificity of the drug to only some of the cell lines.

Results for the 1-dose 60 cell testing at $10^{-5}$ M of RL-1, RL-2, RL-3 and RL-4 are presented in FIGS. 1 through 4. RL-1, RL-2 and RL-3 show little to no effect on cell growth, with all three compounds having average growth percentages across all cell lines essentially 100%. The mean growth percentages (and Delta) for these three compounds are 104.31 (Delta=11.75) for RL-1; 99.96 (Delta=30.65) for RL-2, and 101.11 (Delta=24.63) for RL-3. If the 50% growth percentage criterion is applied, RL-1, RL-2 and RL-3 show little to no growth inhibition or anti-proliferative efficacy against cancer cell lines at the $10^{-5}$ M concentration.

By contrast to RL-1, RL-2, and RL-3, RL-4 shows significant growth inhibition in almost all cell lines, having a Mean Growth Percent of 59.94% (Delta=52.07).

The range of Growth Percentage for RL-4 is quite large, from 7.87 for SK-MEL-5 (Melanoma) to 129.23 for MCA-MB-231/ATCC (Breast) resulting in a Range=121.36. Only 6 cell lines exhibit Growth Percentages greater than 90%, indicating no significant or no growth inhibition of RL-4 on these cell lines: These 6 cells lines (and Growth Percentages) are NCI-H552 (non-small cell lung cancer, 91.26%), SK-MEL-28 (Melanoma, 93.53%), SN12C (Renal Cancer, 95.87%), MALME-3M (Melanoma, 98.97%), for TK-10 (Renal Cancer, 120.12%), and MDA-MB-231/ATCC (Breast, 129.23%). Specificity appears related to individual cell lines, rather than cancer types or panels. If the 50% growth percentage criterion is applied, RL-4 shows growth inhibition in 22 of the 60 cell lines tested at the $10^{-5}$ M dosage.

RL-4 shows no toxicity: All cell-line specific Growth percentages are positive, indicating that there is no cell lethality at the $10^{-5}$ M dosage.

The 5-dose 60 cell assay was performed for RL-4.

The percentage growth is calculated at each of the five drug concentrations levels using the seven absorbance measurements, namely absorbance at time zero (Tz), absorbance of control after incubation (C), and absorbance of test sample after incubation in the presence of drug at each of the five concentration levels (Ti). The Growth Percent is calculated as it was for the 1 dose assay:

Growth Percent=[(Ti−Tz)/(C−Tz)]×100 for cell line/
  drug combinations for which Ti≥Tz.

Growth Percent=[(Ti−Tz)/Tz]×100 for cell line/drug
  combinations for which Ti<Tz.

For the 5-dose 60 cell testing, three dose-response parameters are determined for each experimental agent. These parameters are Growth Inhibition of 50% (GI50), drug concentration resulting in Total Growth Inhibition (TGI), and concentration resulting in 50% lethality (LC50).

Growth inhibition of 50% (GI50) is determined as the drug concentration at which Growth Percent=[(Ti−Tz)/(C−Tz)]×100=50. GI50 is the drug concentration resulting in a 50% reduction in the net protein increase compared to the increase in protein in control cells (as measured by SRB staining) during the drug incubation.

The drug concentration resulting in total growth inhibition (TGI) is determined as the drug concentration at which Ti=Tz, which corresponds to a Growth Percent of zero.

The LC50 (concentration of drug resulting in a 50% reduction in the measured protein at the end of the drug treatment as compared to that at the beginning) is the drug concentration at which Growth Percent=[(Ti−Tz)/Tz]×100=−50 and indicates a net loss of cells during the incubation, or the concentration of drug that is lethal to 50% of the cells.

Drug concentration values are determined for each of these three parameters if the level of activity is reached; however, if the effect is not reached or is exceeded within the range of drug concentrations tested, the value for that parameter is expressed as greater or less than the maximum or minimum drug concentration tested.

Results for the 5-dose 60 cell testing of RL-4 (one repeat of the bioassay) are presented in FIGS. 5 through 7.

RL-4 shows significant growth inhibition across all 60 cell lines at some level of dosage tested. The Mean GI50 is $2 \times 10^{-5}$ M, with $\log_{10}$GI50 Mean=−5.0, Delta=1.45, Range=2.45, FIG. 7.

For only two cell lines was the GI50 higher that the $10^{-4}$ M concentration of RL-4 tested: NCI-H322M (non-small cell lung cancer) showed 60% growth percent at the $10^{-4}$ M dose of RL-4, and OVCAR-5 (ovarian cancer) showed 54% growth percent at the $10^{-4}$ M dose of RL-4-both significant growth inhibitions but not meeting the 50% criterion.

In eight cell lines, total growth inhibition (growth percent=0) was achieved within the dosage range tested and TGI concentrations determined, FIG. 7.

In only one case, COLO 205 (Colon Cancer) was the growth percent less than −50, that is 50% or more of the cells died. For COLO 205, the LC50 was determined as $8.575 \times 10^{-5}$ M RL-4. For all other cell lines, the LC50 is $>10^{-4}$ M RL-4, that is, RL-4 is not toxic at the concentrations tested, up to $10^{-4}$ M.

RL-4 shows specificity to individual cell lines, FIGS. 5, 6 and 7. The range of GI50 is large, from $3.53 \times 10^{-7}$ M for MCF7 (Breast Cancer) to $>10^{-4}$ M for both NCI-H322M (non-small cell lung cancer) and OVCAR-5 (ovarian cancer), FIG. 5. Responses within each panel, that is, type of cancer, are quite varied, indicating little specificity to panels or types of cancer, only to specific cell lines.

In summary, RL-4 shows anti-proliferative efficacy across a range of 60 cell lines encompassing nine panels or cancer cell types. Within the range of concentrations tested, RL-4 showed cytostatic activity (TGI=0) for eight of the 60 cell lines tested. Toxicity, as defined by LC50, is not observed for RL-4 at concentrations up to $10^{-4}$ M in any of the cell lines except for COLO 205.

In vitro characterizing of the effects of rilyazine analogs on cell proliferation and apoptosis in the paired epithelial/mesenchymal lines (Colo205/Colo-R, DLD/DLD-SNAIL and MCF7/MCF7-WISP) was performed in an independent laboratory.

The Dose Preparation is based on a reconstitute in DMSO. The Concentration of the stock solution is 100 mM. Storage of the stock solution is under −80° C.

Working drug solution of rilyazine analogs: A stock solution of 100 mM OTX015 in DMSO was prepared and stored at −80° C. For growth inhibition studies, dilution series were prepared by (1) diluting stock solution into DMSO, then (2) diluting 1:300 in culture medium supplemented with 10% FBS giving a final concentration in 0.3% DMSO in the 96-well plates.

Compound di-2-pyridylketone 4-cyclohexyl-4-methyl-3-thiosemicarbazone, which is not in the Rilyazine class of compounds but was identified as RL-5 in FIGS. 8-11, is used as a positive control.

Cell lines. Cells lines were maintained in RPMI 1640 (PAA Laboratories, France) supplemented with 10% fetal bovine serum (FBS; PAA Laboratories, France), 2 mM glutamine (PAA Laboratories, France), 100 units/ml penicillin and 100 μg/ml streptomycin (PAA Laboratories, France). Cells were free of Mycoplasma.

| Colon | Colo-205 | Parental cell line -Ephitelial cell line- |
| Breast | MCF-7 | Parental cell line -Ephitelial cell line- |
| Breast | MCF-shWISP | Mesenchymal cell line |

Proliferation assays. Cell proliferation was determined using the MTT assay (3-[4,5-dimethylthiazol-2-yl]-2,5-diphenyltetrazolium bromide; Sigma-Aldrich, St. Louis, Mo.). The conversion of yellow water-soluble tetrazolium MTT into purple insoluble formazan was catalyzed by mitochondrial dehydrogenases and used to estimate the number of viable cells. Cells were seeded in 96-well tissue culture plates at a density of $2.10^3$ cells/well. After 72 h-drug exposure at different drug concentrations, cells were incubated with 0.4 mg/ml MTT for 4 hours at 37° C. After incubation, the supernatant was discarded, the cell pellet was resuspended in 0.1 mL DMSO, and the absorbance was measured at 560 nm using a microplate reader (Thermo, France). Wells with DMSO 0.3% were used as negative controls. Assays were performed in triplicate.

For the evaluation of the anti-proliferative effects of the Rilyazine analogs, the range of concentrations employed was between 30-0.041 μM, and also between 3.3 μM-1.51 nM. See Lovejoy D, *J. Med. Chem.* 2012, 55, 7230-7244. *Novel Second-Generation Di-2-Pyridylketone Thiosemicarbazones Show Synergism with Standard Chemotherapeutics and Demonstrate Potent Activity against Lung Cancer Xenografts after Oral and Intravenous Administration in Vivo.*

RL-4 displayed dose-dependent anti-proliferative effects in the three cellular models. After 72 h-exposure, the remainders compounds did not exert anti-proliferative effects in Colo-205, MCF-7 and MCF-shWISP cells in the evaluated concentrations range (30-0.041 μM) (FIGS. 8 and 9).

As negative control was employed 0.3% DMSO and Docetaxel as positive control, which GI50 values were similar to those obtained in previous experiments in our lab (FIG. 8 and FIG. 9).

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

The entire disclosures of all documents cited throughout this application are incorporated herein by reference.

What is claimed is:
1. A compound selected from the group consisting of:

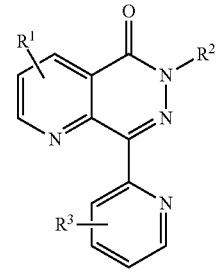

RL-A

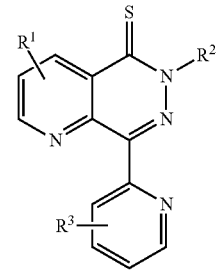

RL-B

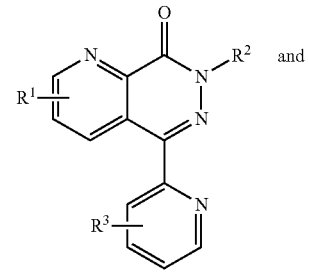

RL-C and

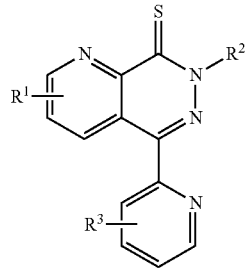

RL-D wherein:
each $R^1$ is independently selected from the group consisting of hydrogen, halo, nitro, trifluoromethyl, trifluoromethoxy, methoxy, carboxy, —NH$_2$, —OH, —SH, —NHCH$_3$, —N(CH3)2, —SCH3, —CN, (C$_1$-C$_6$)alkyl, substituted (C$_1$-C$_6$)alkyl, aryl and heteroaryl;

each $R^2$ is independently selected from the group consisting of hydrogen, (C$_1$-C$_{12}$)alkyl, (C$_1$-C$_{12}$)alkoxy, —C(O)(C$_1$-C$_{12}$)alkyl, (C$_3$-C$_{10}$)cycloalkyl, aryl, aryloxy, heteroaryl and heteroaryloxy, wherein each of (C$_1$-C$_{12}$)alkyl, (C$_1$-C$_{12}$)alkoxy, —C(O)(C$_1$-C$_{12}$)alkyl, (C$_3$-C$_{10}$)cycloalkyl, aryl, aryloxy, heteroaryl and heteroaryloxy is unsubstituted or substituted with 1 or 2 substituents selected from the group consisting of halo, nitro, trifluoromethyl, trifluoromethoxy, methoxy, carboxy, —NH$_2$, —OH, —SH, —NHCH$_3$, —N(CH$_3$)$_2$, -SCH$_3$, —CN, (C$_1$-C$_6$)alkyl, substituted (C$_1$-C$_6$)alkyl, aryl and heteroaryl; and each R³ is independently selected from the group consisting of hydrogen, halo, nitro, trifluoromethyl, trifluoromethoxy, methoxy, carboxy, —NH₂, —OH, —SH, —NHCH₃, —N(CH₃)₂, —SCH₃, —CN, (C₁-C₆)alkyl, substituted (C₁-C₆)alkyl, aryl and heteroaryl;

as a single stereoisomer, a mixture of stereoisomers, and a pharmaceutically acceptable salt thereof.

2. The compound of claim 1, wherein:

each R² is independently selected from the group consisting of (C₁-C₁₂)alkyl, (C₁-C₁₂)alkyl-aryl, (C₁-C₁₂)alkoxy, —C(O)(C₁-C₁₂)alkyl, (C₃-C₁₀)cycloalkyl, aryl and heteroaryl, wherein each of (C₁-C₁₂)alkyl, (C₁-C₁₂)alkoxy, —C(O)(C₁-C₁₂)alkyl, (C₃-C₁₀)cycloalkyl, aryl and heteroaryl is unsubstituted or substituted with 1 or 2 substituents selected from the group consisting of halo, nitro, trifluoromethyl, trifluoromethoxy, methoxy, carboxy, —NH₂, —OH, —SH, —NHCH₃, —N(CH₃)₂, -SCH₃, —CN, (C₁-C₆)alkyl, substituted (C₁-C₆)alkyl, aryl and heteroaryl.

3. The compound of claim 2, wherein:

R¹ and R³ are each hydrogen; and each R² is independently selected from the group consisting of —CH₂CH₃, -cyclohexyl, —CH₂C₆H₅, -phenyl, -2-pyridinyl and -CH₂-2-pyridinyl.

4. The compound of claim 1 wherein:

the compound is RL-D;

R¹ and R³ are each hydrogen; and each R² is independently selected from the group consisting of (C₁-C₁₂)alkyl, (C₁-C₁₂)alkyl-aryl, (C₁-C₁₂)alkoxy, —C(O)(C₁-C₁₂)alkyl, (C₃-C₁₀)cycloalkyl, aryl and heteroaryl, wherein each of (C₁-C₁₂)alkyl, (C₁-C₁₂)alkoxy, —C(O)(C₁-C₁₂)alkyl, (C₃-C₁₀)cycloalkyl, aryl and heteroaryl is unsubstituted or substituted with 1 or 2 substituents selected from the group consisting of halo, nitro, trifluoromethyl, trifluoromethoxy, methoxy, carboxy, —NH₂, —OH, —SH, —NHCH₃, —N(CH₃)₂, —SCH₃, —CN, (C₁-C₆)alkyl, substituted (C₁-C₆)alkyl, aryl and heteroaryl.

5. The compound of claim 1, wherein:

R¹ and R³ are each hydrogen; and each R² is independently selected from the group consisting of:

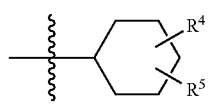

wherein R⁴ and R⁵ are each independently hydrogen, (C₁-C₆)alkyl, F, Cl, Br, I, nitro, trifluoromethyl, trifluoromethoxy, methoxy, carboxy, —NH₂, —OH, —SH, —NHCH₃, —N(CH₃)₂, —SCH₃ and —CN.

6. The compound of claim 5, wherein:

R⁴ is hydrogen; and

R⁵ is 2-, 3- or 4-substituted with (C₁-C₃)alkyl;

as a single isomer or mixture of stereoisomers.

7. The compound of claim 1 selected from the group consisting of:

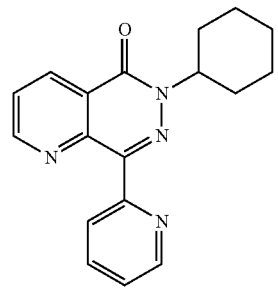
RL-1

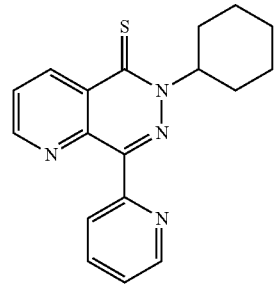
RL-2

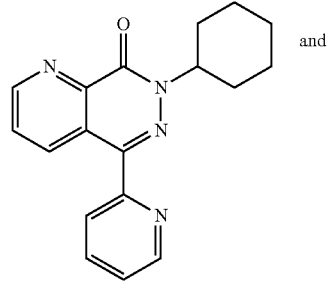
RL-3
and

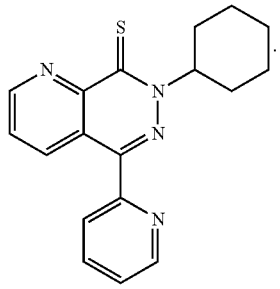
RL-4

8. The compound of claim 7, wherein the compound is:

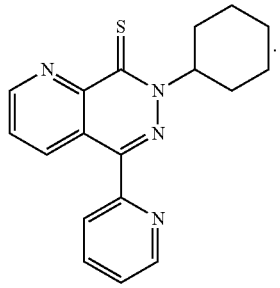
RL-4

9. A pharmaceutical composition comprising a therapeutically effective amount of a compound of claim 1, and a pharmaceutically acceptable excipient.

\* \* \* \* \*